United States Patent
Manetsch et al.

(10) Patent No.: US 10,067,136 B1
(45) Date of Patent: Sep. 4, 2018

(54) PHOTOACTIVATABLE PROBES AND USES THEREOF

(71) Applicants: Roman Manetsch, Boston, MA (US); Arun Babu Kumar, Bothell, WA (US); Jeremiah Tipton, Knoxville, TN (US)

(72) Inventors: Roman Manetsch, Boston, MA (US); Arun Babu Kumar, Bothell, WA (US); Jeremiah Tipton, Knoxville, TN (US)

(73) Assignee: University of South Florida, Tampa, FL (US)

( * ) Notice: Subject to any disclaimer, the term of this patent is extended or adjusted under 35 U.S.C. 154(b) by 0 days.

(21) Appl. No.: 15/425,275

(22) Filed: Feb. 6, 2017

Related U.S. Application Data

(60) Provisional application No. 62/291,983, filed on Feb. 5, 2016.

(51) Int. Cl.
| | |
|---|---|
| *C07D 401/04* | (2006.01) |
| *C07D 403/04* | (2006.01) |
| *G01N 33/58* | (2006.01) |
| *C07D 495/04* | (2006.01) |
| *C07H 15/26* | (2006.01) |
| *C07K 1/13* | (2006.01) |
| *G01N 33/68* | (2006.01) |

(52) U.S. Cl.
CPC ............ *G01N 33/58* (2013.01); *C07D 401/04* (2013.01); *C07D 403/04* (2013.01); *C07D 495/04* (2013.01); *C07H 15/26* (2013.01); *C07K 1/13* (2013.01); *G01N 33/6848* (2013.01)

(58) Field of Classification Search
None
See application file for complete search history.

(56) References Cited

PUBLICATIONS

Kumar, et al., Chem. Comm., 52:2729. (Year: 2016).*
Raimer, et al., Eur. J. Org. Chem., 25:5509. (Year: 2014).*
J. Das, Chem. Rev. 2011, 111, 4405-4417.
Z. Li, et al., J. Am. Chem. Soc. 2014, 136, 9990-9998.
Y. Hatanaka, Y. Sadakane, Cum Top. Med. Chem. 2002, 2, 271-288.
F. Kotzybahibert, I. Kapfer, M. Goeldner, Angew. Chem. Int. Ed. Engl. 1995, 34, 1296-1312.
C. A. Gartner, Curr. Med. Chem. 2003, 10, 671-689.
H. Nakayama, Y. Hatanaka, M. Taki, E. Yoshida, Y. Kanaoka, Ann. N. Y. Acad. Sci. 1993, 707, 349-351.
J. Yang, A. E Clark, I. J. Kozka, S. W. Cushman, G. D. Holman, J. Biol. Chem. 1992, 267, 10393-10399.
J. J. Tate, J. Persinger, B. Bartholomew, Nucleic Acids Res. 1998, 26, 1421-1426.
P. J. A. Weber, A. G. BeckSickinger, J. Pept. Res. 1997, 49, 375-383.
M. Hashimoto, Y. Hatanaka, Eur. J. Org. Chem. 2008, 2008, 2513-2523.
L. Dubinsky, B. P. Krom, M. M. Meijler, Bioorg. Med. Chem. 2012, 20, 554-570.
B. L. Liu, D. S. Kang, J. Chem. Inf. Comput. Sci., 1994, 34, 418-420.
Y. G. He, C. P. Junk, J. J. Cawley, D. M. Lemal, J. Am. Chem. Soc. 2003, 125, 5590-5591.
J. E. True, T. D. Thomas, R. W. Winter, G. L.Gard, Inorg Chem 2003, 42, 4437-4441.
J. Brunner, H. Senn, F. M. Richards, J. Biol. Chem. 1980, 255, 3313-3318.
B. Emi, H. G. Khorana, J. Am. Chem. Soc. 1980, 102, 3888-3896.
R. Bonneau, M. T. H. Liu, J. Am. Chem. Soc. 1996, 118, 7229-7230.
T. Akasaka, M. T. H. Liu, Y. Niino, Y. Maeda, T. Wakahara, M. Okamura; K. Kobayashi, S. Nagase, J. Am. Chem. Soc. 2000, 122, 7134-7135.
T. Wakahara, Y. Niino, T. Kato, Y. Maeda, T. Akasaka, M. T. H. Liu, K. Kobayashi, S. Nagase, J. Am. Chem. Soc. 2002, 124, 9465-9468.
R. A. Moss, E. G. Jang, H. R. Kim, G. J. Ho, M. S. Baird, Tetrahedron Lett. 1992, 33, 1427-1430.
R. A. Moss, L. A. Perez, N. J. Turro, I. R. Gould, N. P. Hacker, Tetrahedron Lett. 1983, 24, 685-688.
N. Soundararajan, M. S. Platz, J. E. Jackson, M. P. Doyle, S. M. Oon, M. T. H. Liu, S. M. Anand, J. Am. Chem. Soc. 1988, 110, 7143-7152.
Hasnik, Z.; Silhar, P.; Hocek, M., Hydroxymethylations of aryl halides by Pd-catalyzed cross-couplings with (benzoyloxy)methylzinc iodide—Scope and limitations of the reaction. Synlett 2008, 543-546.
S. S. Husain, S. Nirthanan, D. Ruesch, K. Solt, Q. Cheng, G. D. Li, E. Arevalo, R. W. Olsen, D. E. Raines, S. A. Forman, J. B. Cohen, K. W. Miller, J. Med. Chem. 2006, 49, 4818-4825.
A. B. Kumar, J. M. Anderson, R. Manetsch, Org. Biomol. Chem. 2011, 9, 6284-6292.
M. Daghish, L. Hennig, M. Findeisen, S. Giesa, F. Schumer, H. Hennig, A. G. Beck-Sickinger, P. Welzel, Angew. Chem. Int. Ed. Engl. 2002, 41, 2293-2297.
Y. L. Zhang, G. Burdzinski, J. Kubicki, S. Vyas, C. M. Hadad, M. Sliwa, O. Poizat, G. Buntinx, M. S. Platz, J. Am. Chem. Soc. 2009, 131, 13784-13790.
Cross, R. M.; Monastyrskyi, A.; Mukta, T. S.; Burrows, J. N.; Kyle, D. E.; Manetsch, R., Endochin Optimization: Structure-Activity and Structure-Property Relationship Studies of 3-Substituted 2-Methyl-4(1H)-quinolones with Antimalarial Activity. Journal of Medicinal Chemistry 2010, 53, 7076-7094.
T. Nagase, E. Nakata, S. Shinkai, I. Hamachi, Chem. Eur. J. 2003, 9, 3660-3669.
K. S. Van Horn, W. N. Burda, R. Fleeman, L. N. Shaw, R. Manetsch, J. Med. Chem. 2014, 57, 3075-3093.
R. M. Cross, D. L. Flanigan, A. Monastyrskyi, A. N. LaCrue, F. E. Sáenz, J. R. Maignan, T. S. Mutka, K. L White, D. M. Shackleford, (Continued)

*Primary Examiner* — Michael Barker
(74) *Attorney, Agent, or Firm* — Thomas | Horstemeyer, LLP

(57) ABSTRACT

Provided herein are pyridyl- and pyrimidyl-containing diazirines that can be photoactivateable probes and formulations thereof. Also provided herein are photoaffinity labels that can include the pyridyl- and pyrimidyl-containing diazirines provided herein. Also provided herein are methods of using the photoactivatable probes and photoaffinity labels provided herein in a photoaffinity labeling reaction and/or assay.

20 Claims, 17 Drawing Sheets

(56) References Cited

PUBLICATIONS

I. Bathurst, F. R. Fronczek, L. Wojtas, W. C. Guida, S. A. Charman, J. N. Burrows, D. E. Kyle, R. Manetsch, J. Med. Chem. 2014, 57, 8860-8879.
K. S. Van Horn, X. Zhu,; T. Pandharkar, S. Yang, B. Vesely, M. Vanaerschot, J. C. Dujardin, S. Rijal, D. E. Kyle, M. Z. Wang, K. A. Werbovetz, R. Manetsch, J. Med. Chem. 2014, 57, 5141-5156.
Kottani, R.; Valiulin, R. A.; Kutateladze, A. G., Direct screening of solution phase combinatorial libraries encoded with axternally sensitized photolabile tags. Proceedings of the National Academy of Sciences of the United States of America 2006, 103, 13917-13921.
Habermeyer, B.; Takai, A.; Gros, C. P.; El Ojaimi, M.; Barbe, J. M.; Fukuzumi, S., Dynamics of Closure of Zinc Bis-Porphyrin Molecular Tweezers with Copper(II) Ions and Electron Transfer. Chemistry-a European Journal 2011, 17, 10670-10681.
E. Smith, I. Collins, Future Med Chem 2015, 7, 159-183.
G. Dorman, Bioorg. Chem. of Biol. Signal Transduction 2001, 211, 169.

\* cited by examiner

| Duration of ambient light exposure (days) | Amounts of unreacted diazirine (%) | | |
|---|---|---|---|
| | 3 | 1 | 2 |
| 0 | 100 | 100 | 100 |
| 4 | 87.7 | 97.1 | 99 |
| 7 | 78.1 | 95.2 | 98 |
| 14 | 58.1 | 90.1 | 95.2 |
| 18 | 49 | 87.7 | 94.3 |
| 26 | 35 | 82.6 | 92.6 |
| 31 | 26.8 | 79.4 | 90.1 |

FIG. 7

| Duration of incandescent lamp exposure (days) | Amounts of unreacted diazirine (%) | | |
|---|---|---|---|
| | phenyl | pyridinyl | pyrimidinyl |
| 0 | 100.0 | 100.0 | 100.0 |
| 1 | 94.3 | 97.1 | 98.0 |
| 3 | 85.5 | 93.5 | 96.2 |
| 5 | 74.1 | 87.7 | 91.7 |
| 15 | 22.5 | 54.9 | 67.1 |

FIG. 8

| Compound | Aqueous Solubility (µM) | |
| --- | --- | --- |
| | pH 7.4 | pH 5.0 |
| 14 | < 0.02 | < 0.02 |
| 15 | 4.09 ± 0.19 | 4.29 ± 0.14 |
| 16 | 133 ± 0.5 | 131 ± 1.7 |
| 17 | 11.3 ± 0.55 | 14.1 ± 0.43 |
| 18 | 374 ± 2.7 | 422 ± 4.9 |
| 19 | ≥ 1,000 | ≥ 1,000 |

FIG. 10

| Photo probe | Mass calculated | | | Mass found | | Error in mass accuracy (ppm) |
|---|---|---|---|---|---|---|
| | Mass of peptide Val91 - Lys101 (VGLSASTGLYK) | Mass of (probe -N$_2$) | Mass of (peptide + probe - N$_2$) | Mass of doubly protonated peptide | Mass of neutral peptide | |
| 20 | 1094.5972 | 732.3016 | 1826.8988 | 914.4585 | 1826.9034 | 1.97 |
| 21 | 1094.5972 | 733.2968 | 1827.8940 | 914.9558 | 1827.8970 | 1.64 |
| 22 | 1094.5972 | 734.2921 | 1828.8893 | 915.4543 | 1828.8940 | 2.57 |

| Photo probe | Mass Calculated | | | Mass Found | | Error in mass accuracy (ppm) |
|---|---|---|---|---|---|---|
| | Mass of peptide Val91 - Lys101 (VGLSASTGLYK) | Mass of (probe - N₂ - mannose) | Mass of (peptide + probe - N₂ - mannose) | Mass of doubly protonated peptide | Mass of neutral peptide | |
| 20 | 1094.5972 | 570.2488 | 1664.8460 | 833.4328 | 1664.8510 | 3.00 |
| 21 | 1094.5972 | 571.2440 | 1665.8412 | 833.9284 | 1665.8422 | 0.60 |
| 22 | 1094.5972 | 572.2393 | 1666.8365 | 834.4272 | 1666.8398 | 1.98 |

PHOTOACTIVATABLE PROBES AND USES THEREOF

CROSS-REFERENCE TO RELATED APPLICATIONS

This application claims the benefit of and priority to U.S. Provisional Patent Application No. 62/291,983 filed on Feb. 5, 2016, entitled "3-TRIFLUOROMETHYL-3-ARYLDIAZIRINE PHOTOLABELS WITH ENHANCED AMBIENT LIGHT STABILITY," the contents of which is incorporated by reference herein in its entirety.

STATEMENT REGARDING FEDERALLY SPONSORED RESEARCH OR DEVELOPMENT

This invention was made with government support under grant number R01 GM097118 awarded by the National Institutes of Health. The government has certain rights in the invention.

BACKGROUND

Photoaffinity labeling is an established approach to examine interactions between a ligand and a biological receptor, which relies on a photoactivatable probe (a photolabel) to form a covalent bond between the ligand and the biological receptor upon irradiation, typically with ultra-violet (UV) light, of the ligand-receptor complex. Although many types of photoactivatable groups have been developed over the past 40 years, many suffer from, for example, cumbersome synthesis, instability in ambient light conditions, and limited aqueous solubility. As such, there exists a need for improved photolabels that can be used in photoaffinity labeling techniques.

SUMMARY

Provided herein are compounds that can have a structure according to Formula A

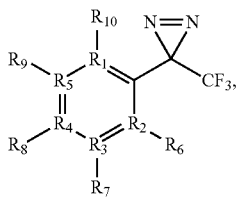

Formula A wherein $R_1$, $R_2$, $R_3$, $R_4$, and $R_5$, can each be independently selected from the group consisting of: C and N, wherein at least one of $R_1$, $R_2$, $R_3$, $R_4$, and $R_5$, is N, wherein $R_6$, $R_7$, $R_8$, $R_9$, and $R_{10}$ can each be independently selected from the group consisting of H, —OH, and an alkyl alcohol, and wherein at least one of $R_6$, $R_7$, $R_8$, $R_9$, and $R_{10}$ can be an —OH or an alkyl alcohol. In some embodiments, at least two of $R_1$, $R_2$, $R_3$, $R_4$, and $R_5$, can be N. In some embodiments, $R_3$, and $R_5$, can be N. In some embodiments, $R_8$ can be an alkyl alcohol. In some embodiments, the compound can have a structure according to Formula 2

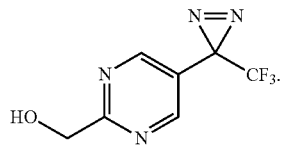

Formula 2

In some embodiments, $R_5$, is N. In some embodiments where $R_5$, is N, $R_8$ can be an alkyl alcohol.

In some embodiments, the compound can have a structure according to Formula 1

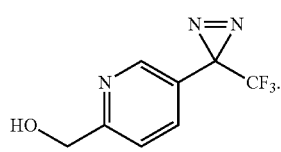

Formula 1

Also provided herein are methods of preparing a photoaffinity label. The methods can provide the step of comprising coupling a photoaffinity tag to a compound having a structure according to Formula A

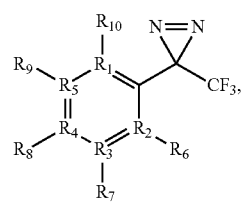

Formula A wherein $R_1$, $R_2$, $R_3$, $R_4$, and $R_5$, can each be independently selected from the group consisting of: C and N, wherein at least one of $R_1$, $R_2$, $R_3$, $R_4$, and $R_5$, is N, wherein $R_6$, $R_7$, $R_8$, $R_9$, and $R_{10}$ can each be independently selected from the group consisting of H, —OH, and an alkyl alcohol, and wherein at least one of $R_6$, $R_7$, $R_8$, $R_9$, and $R_{10}$ can be an —OH or an alkyl alcohol. In some embodiments, at least two of $R_1$, $R_2$, $R_3$, $R_4$, and $R_5$, can be N. In some embodiments, $R_3$, and $R_5$, can be N. In some embodiments, $R_8$ can be an alkyl alcohol. In some embodiments, the compound having a structure according to Formula A can have a structure according to Formula 2

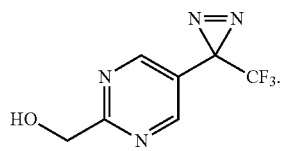

Formula 2

In some embodiments, $R_5$, can be N. In some embodiments where $R_5$, can be N, $R_8$ can be an alkyl alcohol. In some embodiments, the compound that can have structure according to Formula A has a structure according to Formula 1

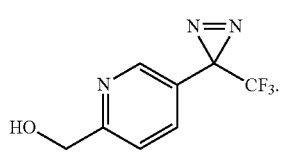

Formula 1

In some embodiments, the method can further include the step of coupling a ligand of a protein to the compound having a structure according to Formula A. The method can further include the step of contacting the compound having a structure according to Formula A that is coupled to a photoaffinity tag and ligand with a protein. In some embodiments, the method can further include the step of coupling a protein to the compound having a structure according to Formula A. In some embodiments, the photoaffinity tag can be selected from the group of: biotin, His-tag, FLAG, Streptag II, hemagllutinin (HA)-tag, Softag1, Softag3, c-myc, T7-tag, S-tag, Elastin-like peptides, Chitin-binding domain, Thioredoxin, Xylanase 10A, Glutathione S-transferase, Maltose binding protein, NusA, any amine derivative thereof, and any combinations thereof.

BRIEF DESCRIPTION OF THE DRAWINGS

Further aspects of the present disclosure will be readily appreciated upon review of the detailed description of its various embodiments, described below, when taken in conjunction with the accompanying drawings.

FIG. 5B shows a virtual docking of the native ligand mannose bound to Con A (PDB ID: 3CNA). Note that peptide Val91-Lys101 (VGLSASTGLYK) (highlighted in purple) has been labeled by the photoaffinity probes 20-22, which indicates that photoprobes 20-22 are binding and labeling the protein at the saccharide binding sites of Con A.

FIG. 7 shows a table demonstrating a comparison of ambient light stability of modified trifluoromethylaryl diazirines 1 and 2 versus the conventional trifluoromethylphenyl diazirine. A solution of trifluoromethylaryl diazirines 1, 2 or 3 in d4-methanol was exposed to light from two linear fluorescent lamps (28 W each) at room temperature and the photodecomposition of the diazirines were followed by $^{19}F$ NMR. Percentage of diazirine intact upon exposure to ambient light at various time intervals.

FIG. 8 shows a table demonstrating a comparison of stability of modified trifluoromethylaryl diazirines 1 and 2 versus the conventional trifluoromethylphenyl diazirine 3 under exposure to incandescent light. Percentage of diazirine intact upon exposure to incandescent light at various time intervals.

FIG. 10 shows a table demonstrating a comparison of aqueous solubility of photoaffinity probes derivatized with modified photolabels 1 and 2 with conventional photolabel 3. The aqueous solubility of the photolabels increased by several orders of magnitude when the phenyl derived diazirine was replaced with the pyridinyl or pyrimidinyl derived diazirine.

DETAILED DESCRIPTION

Figure 1:
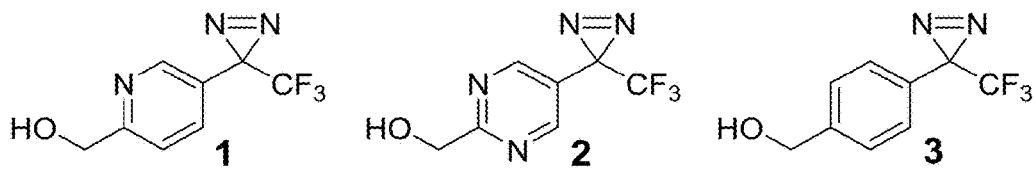
FIG. 1 shows design of ambient light stable pyridine and pyrimidine derived 3-trifluoromethyl-3-aryldiazirines 1 and 2.

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of chemistry, organic chemistry, biochemistry, and the like, which are within the skill of the art. Such techniques are explained fully in the literature.

Definitions

As used herein, "about," "approximately," and the like, when used in connection with a numerical variable, can refer to the value of the variable and to all values of the variable that are within the experimental error (e.g., within the 95% confidence interval for the mean) or within +/−10% of the indicated value, whichever is greater.

As used herein, "additive effect" can refer to an effect arising between two or more molecules, compounds, substances, factors, or compositions that is equal to or the same as the sum of their individual effects.

As used interchangeably herein, "biocompatible," "biocompatibility," and "biologically compatible" can refer to materials that are, with any metabolites or degradation products thereof, generally non-toxic to the recipient, and cause no significant adverse effects to the recipient. Generally speaking, biocompatible materials are materials which do not elicit a significant inflammatory or immune response when administered to a patient. In some embodiments, a biocompatible material elicits no detectable change in one or more biomarkers indicative of an immune response. In some embodiments, a biocompatible material elicits no greater than a 10% change, no greater than a 20% change, or no greater than a 40% change in one or more biomarkers indicative of an immune response.

As used herein, "a compound of formula (1), (2), (3), (4), (5), (6), (6a), (6b) (7), (8), (9), (10), (11), (12), (13), (14), (A), (B), (C), (D), and so forth and so on," or "a compound having a structure according to formula (1), (2), (3), (4), (5), (6), (6a), (6b) (7), (8), (9), (10), (11), (12), (13), (14), (A), (B), (C), (D), etc.," compound (1), (2), (3), (4), (5), (6), (6a), (6b) (7), (8), (9), (10), (11), (12), (13), (14), (A), (B), (C), (D), and so forth and so on," or a "compound" can include all or any sub-group of solvates, complexes, polymorphs, derivatives thereof (including but not limited to, radiolabeled derivatives (including deuterated derivatives where one or more H are replaced by D)), tautomers, stereoisomers, and optical isomers of the compound of the formulas listed above and salts thereof.

As used herein, "control" can refer to an alternative subject or sample used in an experiment for comparison purposes and included to minimize or distinguish the effect of variables other than an independent variable. A control can be positive or negative.

As used herein, "concentrated" can refer to an amount of a molecule, compound, or composition, including, but not limited to, a chemical compound, polynucleotide, peptide, polypeptide, protein, antibody, or fragments thereof, that indicates that the sample is distinguishable from its naturally occurring counterpart in that the concentration or number of molecules per volume is greater than that of its naturally occurring counterpart.

As used herein, "derivative" can refer to substituting, deleting, and/or adding one or more atoms or functional groups. The term "derivative" does not mean that the derivative is synthesized from the parent compound either as a starting material or intermediate, although this may be the case. The term "derivative" can include salts, prodrugs, or metabolites of the parent compound. Derivatives include compounds in which free amino groups in the parent compound have been derivatized to form amine hydrochlorides, p-toluene sulfonamides, benzoxycarboamides, t-butyloxycarboamides, thiourethane-type derivatives, trifluoroacetylamides, chloroacetylamides, or formamides. Derivatives include compounds in which carboxyl groups in the parent compound have been derivatized to form salts, methyl and ethyl esters, or other types of esters or hydrazides. Derivatives include compounds in which a hydrogen bond donating group in the parent compound is replaced with another hydrogen bond donating group such as OH, NH, or SH.

As used herein, "diluted" can refer to an amount of a molecule, compound, or composition including but not limited to, a chemical compound, polynucleotide, peptide, polypeptide, protein, antibody, or fragments thereof, that indicates that the sample is distinguishable from its naturally occurring counterpart in that the concentration or number of molecules per volume is less than that of its naturally occurring counterpart.

As used herein, "hydrate" can refer to a compound formed by the addition of water. Typically, but not always, this will be crystalline lattice structures that incorporate water molecules. Hydrates include stoichiometric hydrates, as well as compositions containing variable amounts of water.

The term "molecular weight", as used herein, can generally refers to the mass or average mass of a material. If a polymer or oligomer, the molecular weight can refer to the relative average chain length or relative chain mass of the bulk polymer. In practice, the molecular weight of polymers and oligomers can be estimated or characterized in various ways including gel permeation chromatography (GPC) or capillary viscometry. GPC molecular weights are reported as the weight-average molecular weight ($M_w$) as opposed to the number-average molecular weight ($M_n$). Capillary viscometry provides estimates of molecular weight as the inherent viscosity determined from a dilute polymer solution using a particular set of concentration, temperature, and solvent conditions.

As used herein, "negative control" can refer to a "control" that is designed to produce no effect or result, provided that all reagents are functioning properly and that the experiment is properly conducted. Other terms that are interchangeable with "negative control" include "sham," "placebo," and "mock."

As used herein, "positive control" can refer to a "control" that is designed to produce the desired result, provided that all reagents are functioning properly and that the experiment is properly conducted.

As used herein, "purified" or "purify" can be used in reference to a nucleic acid sequence, peptide, or polypeptide that has increased purity relative to the natural environment.

As used herein, "separated" can refer to the state of being physically divided from the original source or population such that the separated compound, agent, particle, chemical compound, or molecule can no longer be considered part of the original source or population.

As used herein, "solvate" refers to a complex of variable stoichiometry formed by a solute (e.g. formulas (1)-(1) (A), (B), (C), (D), or any other compound herein or a salt thereof) and a solvent. Pharmaceutically acceptable solvates may be formed for crystalline compounds wherein solvent molecules are incorporated into the crystalline lattice during crystallization. The incorporated solvent molecules can be water molecules or non-aqueous molecules, such as but not limited to, ethanol, isopropanol, dimethyl sulfoxide, acetic acid, ethanolamine, and ethyl acetate molecules.

As used herein, "substantially pure" can mean an object species is the predominant species present (i.e., on a molar basis it is more abundant than any other individual species in the composition), and preferably a substantially purified fraction is a composition wherein the object species comprises about 50 percent of all species present. Generally, a substantially pure composition will comprise more than about 80 percent of all species present in the composition, more preferably more than about 85%, 90%, 95%, and 99%. Most preferably, the object species is purified to essential homogeneity (contaminant species cannot be detected in the composition by conventional detection methods) wherein the composition consists essentially of a single species.

As used herein, "synergistic effect," "synergism," or "synergy" can refer to an effect arising between two or more molecules, compounds, substances, factors, or compositions that that is greater than or different from the sum of their individual effects.

As used herein, "alkyl" and "alkylene" refer to a saturated hydrocarbon chain having the specified number of member atoms.

The term "alkyl" can also refer to the radical of saturated aliphatic groups (i.e., an alkane with one hydrogen atom removed), including straight-chain alkyl groups, branched-chain alkyl groups, cycloalkyl (alicyclic) groups, alkyl-substituted cycloalkyl groups, and cycloalkyl-substituted alkyl groups. "Alkyl" can also refer to a saturated hydrocarbon chain having the specified number of atoms.

The term "alkyl" (or "lower alkyl") as used herein can include both "unsubstituted alkyls" and "substituted alkyls," the latter of which refers to alkyl moieties having one or more substituents replacing a hydrogen on one or more carbons of the hydrocarbon backbone. Such substituents include, but are not limited to, halogen, hydroxyl, carbonyl (such as a carboxyl, alkoxycarbonyl, formyl, or an acyl), thiocarbonyl (such as a thioester, a thioacetate, or a thioformate), alkoxyl, phosphoryl, phosphate, phosphonate, phosphinate, amino, amido, amidine, imine, cyano, nitro, azido, sulfhydryl, alkylthio, sulfate, sulfonate, sulfamoyl, sulfonamido, sulfonyl, heterocycle, aralkyl, or an aromatic or heteroaromatic moiety.

Unless the number of carbons is otherwise specified, "lower alkyl" as used herein can refer to an alkyl group, as defined above, but having from one to ten carbons in its backbone structure. Likewise, "lower alkenyl" and "lower alkynyl" have similar chain lengths.

It will be understood by those skilled in the art that the moieties substituted on the hydrocarbon chain can themselves be substituted, if appropriate. For instance, the substituents of a substituted alkyl may include halogen, hydroxy, nitro, thiols, amino, azido, imino, amido, phosphoryl (including phosphonate and phosphinate), sulfonyl (including sulfate, sulfonamido, sulfamoyl and sulfonate), and silyl groups, as well as ethers, alkylthios, carbonyls (including ketones, aldehydes, carboxylates, and esters), —$CF_3$, —CN and the like. Cycloalkyls can be substituted in the same manner.

As used herein, "alkyl alcohol" can refer to an alkyl having a hydroxyl group. An alkyl alcohol can have the general formula $C_nH_{2n+1}OH$, where n can be any integer of 1 or greater. In some embodiments, the n can be integer from 1-10.

As used herein, "$C_{1-6}$alkyl" can refer to an alkyl group having any number of member atoms from 1 to 6 member atoms, such as for example 1 to 4 atoms. Other alkyl groups may have any number of member atoms as indicated by the numbers given in the formula, which, like the previous example, can refer to an alkyl group having any number of member atoms within the specified range of member atoms. Alkyl groups may be straight or branched. Representative branched alkyl groups have one, two, or three branches. Alkyl includes methyl, ethyl, propyl (n-propyl and isopropyl), butyl (n-butyl, isobutyl, and t-butyl), pentyl (n-pentyl, isopentyl, and neopentyl), and hexyl.

As used herein, "heterocyclic group" can refer to a non-aromatic ring and having the specified number of member atoms being saturated or having one or more degrees of unsaturation and, unless otherwise specified, containing one or more heteroatoms.

As used herein, "heteroaryl" can refer to an aromatic ring having the specified number of member atoms and, unless otherwise specified, containing one or more heteroatoms. Bicyclic and other polycyclic ring systems having a heteroaryl ring are described as fused systems.

The term "heteroalkyl," as used herein, can refer to straight or branched chain, or cyclic carbon-containing radicals, or combinations thereof, containing at least one heteroatom. Suitable heteroatoms include, but are not limited to, O, N, Si, P, Se, B, and S, wherein the phosphorous and sulfur atoms are optionally oxidized, and the nitrogen heteroatom is optionally quaternized. Heteroalkyls can be substituted as defined above for alkyl groups.

The term "heteroalkyl," as used herein, can refer to straight or branched chain, or cyclic carbon-containing radicals, or combinations thereof, containing at least one heteroatom. Suitable heteroatoms include, but are not limited to, O, N, Si, P, Se, B, and S, wherein the phosphorous and sulfur atoms are optionally oxidized, and the nitrogen heteroatom is optionally quaternized. Heteroalkyls can be substituted as defined above for alkyl groups.

As used herein, "alkoxyl" or "alkoxy," as used herein, can refer to an alkyl group, as defined above, having an oxygen radical attached thereto. Representative alkoxyl groups include methoxy, ethoxy, propyloxy, tert-butoxy and the like. An "ether" is two hydrocarbons covalently linked by an oxygen. Accordingly, the substituent of an alkyl that renders that alkyl is an ether or resembles an alkoxyl, such as can be represented by one of —O-alkyl, —O-alkenyl, and —O-alkynyl. The terms "aroxy" and "aryloxy", as used interchangeably herein, can be represented by —O-aryl or O-heteroaryl, wherein aryl and heteroaryl are as defined below. The alkoxy and aroxy groups can be substituted as described above for alkyl.

As used herein, "amine" and "amino" (and its protonated form) are art-recognized and refer to both unsubstituted and substituted amines, e.g., a moiety that can be represented by the general formula:

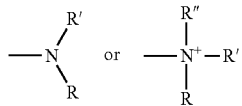

wherein R, R', and R" each independently represent a hydrogen, an alkyl, an alkenyl, —(CH2)$_m$-R$_C$ or R and R' taken together with the N atom to which they are attached complete a heterocycle having from 4 to 8 atoms in the ring structure; R$_C$ represents an aryl, a cycloalkyl, a cycloalkenyl, a heterocycle or a polycycle; and m is zero or an integer in the range of 1 to 8. In some embodiments, only one of R or R' can be a carbonyl, e.g., R, R' and the nitrogen together do not form an imide. In other embodiments, the term "amine" does not encompass amides, e.g., wherein one of R and R' represents a carbonyl. In further embodiments, R and R' (and optionally R") each independently represent a hydrogen, an alkyl or cycloakly, an alkenyl or cycloalkenyl, or alkynyl. Thus, the term "alkylamine" as used herein means an amine group, as defined above, having a substituted (as described above for alkyl) or unsubstituted alkyl attached thereto, i.e., at least one of R and R' is an alkyl group.

As used herein, "amido" is art-recognized as an amino-substituted carbonyl and includes a moiety that can be represented by the general formula:

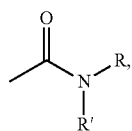

wherein R and R' are as defined above.

As used herein, "Aryl" can refer to C$_5$-C$_{10}$-membered aromatic, heterocyclic, fused aromatic, fused heterocyclic, biaromatic, or bihetereocyclic ring systems. Broadly defined, "aryl", as used herein, includes 5-, 6-, 7-, 8-, 9-, and 10-membered single-ring aromatic groups that may include from zero to four heteroatoms, for example, benzene, pyrrole, furan, thiophene, imidazole, oxazole, thiazole, triazole, pyrazole, pyridine, pyrazine, pyridazine, pyrimidine, and the like. Those aryl groups having heteroatoms in the ring structure may also be referred to as "aryl heterocycles" or "heteroaromatics." The aromatic ring can be substituted at one or more ring positions with one or more substituents including, but not limited to, halogen, azide, alkyl, aralkyl, alkenyl, alkynyl, cycloalkyl, hydroxyl, alkoxyl, amino (or quaternized amino), nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —CF$_3$, —CN, and combinations thereof.

The term "aryl" can also include polycyclic ring systems having two or more cyclic rings in which two or more carbons are common to two adjoining rings (i.e., "fused rings") wherein at least one of the rings is aromatic, e.g., the other cyclic ring or rings can be cycloalkyls, cycloalkenyls, cycloalkynyls, aryls and/or heterocycles. Examples of heterocyclic rings include, but are not limited to, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH carbazolyl, carbolinyl, chromanyl, chromenyl, cinnolinyl, decahydroquinolinyl, 2H,6H-1,5,2-dithiazinyl, dihydrofuro[2,3 b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, and xanthenyl. One or more of the rings can be substituted as defined above for "aryl."

As used herein, "aralkyl," can refer to an alkyl group substituted with an aryl group (e.g., an aromatic or heteroaromatic group).

As used herein, "aralkyloxy" can be represented by —O-aralkyl, wherein aralkyl is as defined above.

As used herein, "carbocycle," can refer to an aromatic or non-aromatic ring(s) in which each atom of the ring(s) is carbon.

As used herein, "heterocycle" or "heterocyclic" can refer to a monocyclic or bicyclic structure containing 3-10 ring atoms, and in some embodiments, containing from 5-6 ring atoms, wherein the ring atoms are carbon and one to four heteroatoms each selected from the following group of non-peroxide oxygen, sulfur, and N(Y) wherein Y is absent or is H, O, ($C_1$-$C_{10}$) alkyl, phenyl or benzyl, and optionally containing 1-3 double bonds and optionally substituted with one or more substituents. Examples of heterocyclic rings include, but are not limited to, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH carbazolyl, carbolinyl, chromanyl, chromenyl, cinnolinyl, decahydroquinolinyl, 2H,6H-1,5,2-dithiazinyl, dihydrofuro[2,3 b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxepanyl, oxetanyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydropyranyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, and xanthenyl. Heterocyclic groups can optionally be substituted with one or more substituents at one or more positions as defined above for alkyl and aryl, for example, halogen, alkyl, aralkyl, alkenyl, alkynyl, cycloalkyl, hydroxyl, amino, nitro, sulfhydryl, imino, amido, phosphate, phosphonate, phosphinate, carbonyl, carboxyl, silyl, ether, alkylthio, sulfonyl, ketone, aldehyde, ester, a heterocyclyl, an aromatic or heteroaromatic moiety, —$CF_3$, —CN, or the like.

The term "carbonyl" is art-recognized and includes such moieties as can be represented by the general formula:

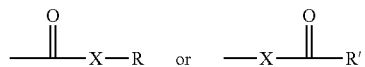

wherein X is a bond or represents an oxygen or a sulfur, and R and R' are as defined above. Where X is an oxygen and R or R' is not hydrogen, the formula represents an "ester". Where X is an oxygen and R is as defined above, the moiety is referred to herein as a carboxyl group, and particularly when R is a hydrogen, the formula represents a "carboxylic acid." Where X is an oxygen and R' is hydrogen, the formula represents a "formate." In general, where the oxygen atom of the above formula is replaced by sulfur, the formula represents a "thiocarbonyl" group. Where X is a sulfur and R or R' is not hydrogen, the formula represents a "thioester." Where X is a sulfur and R is hydrogen, the formula represents a "thiocarboxylic acid." Where X is a sulfur and R' is hydrogen, the formula represents a "thioformate." On the other hand, where X is a bond, and R is not hydrogen, the above formula represents a "ketone" group. Where X is a bond, and R is hydrogen, the above formula represents an "aldehyde" group.

As used herein, "heteroatom" as used herein can refer to an atom of any element other than carbon or hydrogen. Exemplary heteroatoms include, but are not limited to, boron, nitrogen, oxygen, phosphorus, sulfur, silicon, arsenic, and selenium.

As used herein, "nitro" can refer to —$NO_2$; the term "halogen" designates —F, —Cl, —Br, or —I; the term "sulfhydryl" refers to —SH; the term "hydroxyl" refers to —OH; and the term "sulfonyl" refers to —$SO_2$—.

The term "substituted" as used herein, can refer to all permissible substituents of the compounds described herein. In the broadest sense, the permissible substituents can include acyclic and cyclic, branched and unbranched, carbocyclic and heterocyclic, aromatic and nonaromatic substituents of organic compounds. Illustrative substituents include, but are not limited to, halogens, hydroxyl groups, or any other organic groupings containing any number of carbon atoms, e.g. 1-14 carbon atoms, and optionally include one or more heteroatoms such as oxygen, sulfur, or nitrogen grouping in linear, branched, or cyclic structural formats. Representative substituents include alkyl, substituted alkyl, alkenyl, substituted alkenyl, alkynyl, substituted alkynyl, phenyl, substituted phenyl, aryl, substituted aryl, heteroaryl, substituted heteroaryl, halo, hydroxyl, alkoxy, substituted alkoxy, phenoxy, substituted phenoxy, aroxy, substituted aroxy, alkylthio, substituted alkylthio, phenylthio, substituted phenylthio, arylthio, substituted arylthio, cyano, isocyano, substituted isocyano, carbonyl, substituted carbonyl, carboxyl, substituted carboxyl, amino, substituted amino, amido, substituted amido, sulfonyl, substituted sulfonyl, sulfonic acid, phosphoryl, substituted phosphoryl, phosphonyl, substituted phosphonyl, polyaryl, substituted polyaryl, $C_3$-$C_{20}$ cyclic, substituted $C_3$-$C_{20}$ cyclic, heterocyclic, substituted heterocyclic, amino acid, peptide, and polypeptide groups.

Heteroatoms, such as nitrogen, can have hydrogen substituents and/or any permissible substituents of organic compounds described herein which satisfy the valences of the heteroatoms. It is understood that "substitution" or "substituted" includes the implicit proviso that such substitution is in accordance with permitted valence of the substituted atom and the substituent, and that the substitution results in a stable compound, i.e., a compound that does not spontaneously undergo transformation such as by rearrangement, cyclization, elimination, etc.

As used herein, "suitable substituent" can refer to a chemically and pharmaceutically acceptable group, i.e., a moiety that does not significantly interfere with the preparation of or negate the efficacy of the inventive compounds. Such suitable substituents may be routinely chosen by those skilled in the art. Suitable substituents can include, but are not limited to, the following: a halo, $C_1$-$C_6$ alkyl, $C_2$-$C_6$ alkenyl, $C_1$-$C_6$ haloalkyl, $C_1$-$C_6$ alkoxy, $C_1$-$C_6$ haloalkoxy, $C_2$-$C_6$ alkynyl, $C_3$-$C_8$ cycloalkenyl, ($C_3$-$C_8$ cycloalkyl)$C_1$-$C_6$ alkyl, ($C_3$-$C_8$ cycloalkyl)$C_2$-$C_6$ alkenyl, ($C_3$-$C_8$ cycloalkyl) $C_1$-$C_6$ alkoxy, $C_3$-$C_7$ heterocycloalkyl, ($C_3$-$C_7$ heterocycloalkyl)$C_1$-$C_6$ alkyl, (C3-$C_7$ heterocycloalkyl)$C_2$-$C_6$ alkenyl, ($C_3$-$C_7$ heterocycloalkyl)$C_1$-$C_6$ alkoxyl, hydroxy, carboxy, oxo, sulfanyl, $C_1$-$C_6$ alkylsulfanyl, aryl, heteroaryl, aryloxy, heteroaryloxy, arylalkyl, heteroalkyl, arylalkoxy, heteroaralkoxy, nitro, cyano, amino, $C_1$-$C_6$ alkylamino, di-($C_1$-$C_6$ alkyl)amino, carbamoyl, ($C_1$-$C_6$ alkyl)carbonyl, ($C_1$-$C_6$ alkoxy)carbonyl, ($C_1$-$C_6$ alkyl)aminocarbonyl, di-($C_1$-$C_6$ alkyl)aminocarbonyl, arylcarbonyl, aryloxycarbonyl, ($C_1$-$C_6$ alkyl)sulfonyl, and arylsulfonyl. The groups listed above as suitable substituents are as defined hereinafter except that a suitable substituent may not be further optionally substituted.

As used herein, "optionally substituted" can indicate that a group may be unsubstituted or substituted with one or more substituents as defined herein.

Unless otherwise defined herein, all technical and scientific terms used herein have the same meaning as commonly understood by one of ordinary skill in the art.

Discussion

Photoaffinity labeling (PAL) is an established approach to investigate interactions between a ligand and a biological receptor, utilizing a photoactivatable probe to form a covalent bond between the ligand and the biological receptor upon UV light irradiation of the ligand-receptor complex. Many types of photoactivatable groups have been developed over the past 40 years. Some photoactivatable probes can photoreact and form highly reactive intermediates, which can crosslink to a biological receptor.

Ideally, a photoactivatable probe should be readily synthesized, chemically stable and susceptible to smooth photolysis at long wavelengths ($\lambda_{ext} \geq 300$ nm) to exclude photooxidative or other photochemical damage of the biological target. The 3-trifluoromethyl-3-phenyl-diazirine introduced by Brunner is currently the most widely used photolabel. This photolabel produces a singlet carbene as the reactive intermediate, which inserts into carbon-, nitrogen-, oxygen- or sulfur-containing bonds at almost diffusion-controlled reaction rates. Despite the promise of photoactivatable 3H-diazirines as photolabeling agents, the cumbersome synthesis, the instability to ambient light conditions, and the limited aqueous solubility represent major drawbacks for PAL and thus limit its use.

With that said, described herein are 3-pyridyl- and 3-pyrimidyl-substituted 3-trifluoromethyl-diazirines that can be used as photoactivatable probes for photoaffinity labeling techniques. The compounds provided herein can have improved ambient light stability without compromising the photoactivated insertion activity. The compounds provided herein can also have improved aqueous solubility as compared to currently available photoprobes. Other compositions, compounds, methods, features, and advantages of the present disclosure will be or become apparent to one having ordinary skill in the art upon examination of the following drawings, detailed description, and examples. It is intended that all such additional compositions, compounds, methods, features, and advantages be included within this description, and be within the scope of the present disclosure.

Photoactivatable Probes and Formulations Thereof

Provided herein are photactivable probes that can be used for photoaffinity labeling. The photoactivatable probes provided herein can be coupled with a photoaffinity tag and/or a ligand of a protein (e.g. a biological receptor protein) or a protein (e.g. a biological receptor) via one or more coupling reactions. The resulting photoaffinity label can be used to examine, inter alia, the interaction of ligands and their receptor proteins. The pyrmidine and pyrimidyl based photo probes can be more stable in ambient light and can have increased aqueous solubility as compared to conventional phyenl based photoprobes without compromising the photoactivated insertion activity of the photoactiveable probe.

The photoactivateable probe can have a structure according to Formula A

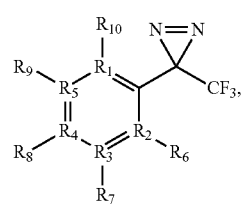

Formula A wherein $R_1$, $R_2$, $R_3$, $R_4$, and $R_5$, can each be independently selected from the group of: C and N, wherein at least one of $R_1$, $R_2$, $R_3$, $R_4$, and $R_5$, can be N, wherein $R_6$, $R_7$, $R_8$, $R_9$, and $R_{10}$ can each be independently selected from the group of H, —OH, and an alkyl alcohol, and wherein at least one of $R_6$, $R_7$, $R_8$, $R_9$, and $R_{10}$ can be an —OH or an alkyl alcohol.

The photoactivateable probe can contain a pyridine. In some embodiments, $R_5$, can be N. In some embodiments, $R_8$ can be an alkyl alcohol. The alkyl alcohol can have between 1 and 6 carbon atoms. The alkyl alcohol can be a linear alkyl alcohol. The photoactivateable probe can have a structure according to Formula 1

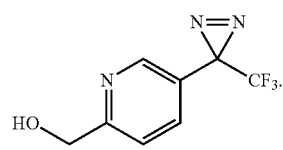

Formula 1

The photoactivatable probe can contain a pyrimidine. In some embodiments, at least two of $R_1$, $R_2$, $R_3$, $R_4$, and $R_5$, can be N. In some embodiments, both $R_3$, and $R_5$, can be N. In some embodiments, $R_8$ can be an alkyl alcohol. The alkyl alcohol can have between 1 and 6 carbon atoms. The alkyl alcohol can be a linear alkyl alcohol. In some embodiments, the photoactivatable probe can have a structure according to Formula 2

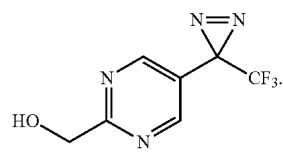

Formula 2

The photoactivateable probes provided herein and derivatives thereof can be synthesized using methods and techniques generally known to those of ordinary skill in the art, including the methods provided herein. The present disclosure is not intended to be limited by the particular methods of synthesizing the compounds described herein. In view of the present disclosure, the skilled artisan can recognize additional methods of synthesizing the compounds provided herein.

In some embodiments, the photoactiveable probes provided herein can have an aqueous solubility of about 4 to 1000 or more μM. In some embodiments the aqueous solubility can be 2 to 1000 fold greater than the conventional phenyl diazirine. In some embodiments, the photoactiveable probes provided herein can be more stable at ambient light and/or incandescent lamp exposure than the conventional phenyl diazirine. The rate of reaction of the photoactivateable probes provided herein in ambient light and/or incandescent lamp exposure can be slower as compared to the conventional phenyl diazirine.

In some embodiments, the photo activateable probes can react at a rate ranging from about 0.4%-0.7% or less per day of the total amount of photoactivateable probe when exposed to ambient light. This is less than the approximately 2.4% or more per day of the total amount of conventional phenyl diazirine based probes when exposed to ambient light. In some embodiments, the photo activateable probes can react at a rate ranging from about 2-3% or less per day of the total amount of photoactivateable probe when exposed to an incandescent lamp. This is far less than the approximately 5% or more per day of the total amount of conventional pheny diazirine based probes after exposure to an incandescent lamp.

Methods of Using the Photoactivatable Probes and Formulations Thereof

The photoactivateable probes provided herein can be used for photoaffinity labeling reactions. The photactivatebale probes can be covalently coupled to a photoaffinity tag and/or a ligand of a protein (e.g. biological receptor) or a protein. As such, provided herein are methods of preparing a photoaffinity label, where the photoaffinity label can include a photactivateable probe as provided herein or a derivative thereof. The methods can include the step of coupling a photoaffinity tag to a photactivateable probe as provided herein. The photoaffinity tag can be covalently coupled to the photactivateable probe. Suitable photoaffinity tags can include, but are not limited to, biotin and derivatives thereof (e.g. biotin, biotin amine, His-tag, FLAG, Streptag II, hemagllutinin (HA)-tag, Softag1, Softag3, c-myc, T7-tag, S-tag, Elastin-like peptides, Chitin-binding domain, Thioredoxin, Xylanase 10A, Glutathione S-transferase, Maltose binding protein, NusA, any amine derivative thereof, and any combinations thereof. See also Arnau et al. (2006) Prot. Expr. Purif. 48:1-13, which is incorporated by reference as if expressed in its entirety, for additional suitable photoaffinity tags).

The methods can further include the step of coupling a ligand or a protein to the photactivateable probe. In some embodiments, both a photoaffinity tag and a ligand or a protein can be coupled to the photoactivateable probe. The photaffinity tag and/or ligand or protein can be coavalently coupled in the same reaction, reaction step, or series of reactions.

The diazarine photoactivateable probe provided herein, ligand or deriviative thereof or a protein or derivative thereof, and/or a photoaffinity tag can be first synthesized as intermediates and coupled together in the final step(s) of a synthesis reaction. In some embodiments, photoactivateable probes that contain a pyridinyl diazirine can be converted into a bromide intermediate via an Apple reaction. In some embodiments, photoactivateable probes that contain a pyrimidinyl diazirine can be reacted with phosphorus tribromide yielded the desired bromide intermediate. After formation of the corresponding bromide intermediate, the bromide intermediate can be treated with an excess of a primary amine to form a secondary amine. In some embodiments, the primary amine is a photoaffinity tag amine (e.g. biotin amine). The secondary amine can be coupled to a ligand or derivitave thereof or a protein or derivative thereof via a suitable coupling reaction (e.g. an EDC reactoin). In some embodiments, the photoaffinity label is formed. Optionally, (such as if a carboxycilic acid derivative of the ligand or protein is used and coupled via an EDC reaction), the product of the prior reaction can be deacetylated via a suitable reaction (e.g. reacting the amide from the prior reaction with a catalytic amount of sodium methoxide in methanol) to yield the final photoaffinity label.

Once the photoaffinity label has been synthesized it can be incubated with and/or come in contact with a protein or a ligand (depending on the photoaffinity label design). The photaffinity label can be activated by stimulation with light, such as ultraviolet light. The ligand or protein of interest can be characterized by a suitable technique such as western blotting. Furthermore, the ligand or protein of interest can also be characterized by suitable bioanalytical mass spectrometry techniques using standard instrumentation such as ion trap, orbitrap, triple quadrupole, time-of-flight and other mass spectrometers.

EXAMPLES

Now having described the embodiments of the present disclosure, in general, the following Examples describe some additional embodiments of the present disclosure. While embodiments of the present disclosure are described in connection with the following examples and the corresponding text and figures, there is no intent to limit embodiments of the present disclosure to this description. On the contrary, the intent is to cover all alternatives, modifications, and equivalents included within the spirit and scope of embodiments of the present disclosure.

Example 1

Introduction

Photoaffinity labeling (PAL) is an established approach to investigate interactions between a ligand and a biological receptor, utilizing a photoactivatable probe to form a covalent bond between the ligand and the biological receptor upon UV light irradiation of the ligand-receptor complex.[1,2] Many types of photoactivatable groups have been developed over the past 40 years, of which 3H-diazirines, arylazides, and benzophenones emerged as the widely used photoprobes.[3,4] 3H-Diazirines, arylazides, and benzophenones photoreact into highly reactive intermediates such as carbenes, nitrenes, and biradicals respectively, which covalently crosslink to a biological receptor.[5]

Ideally, a photoactivatable probe should be readily synthesized, chemically stable and susceptible to smooth photolysis at long wavelengths ($\lambda_{ext} \geq 300$ nm) to exclude photooxidative or other photochemical damage of the biological target. Comparative studies with ion channels,[6] glucose transporter proteins,[7] yeast RNA Polymerase III,[8] and peptide thymopentin[9] identified 3H-diazirines to be best suited for PAL, while arylazides and benzophenones failed at yielding respectable amounts of specific labeling products.[1,10] In particular, the 3-trifluoromethyl-3-phenyldiazirine introduced by Brunner is the most widely used photolabel producing a singlet carbene as the reactive intermediate, which inserts into carbon-, nitrogen-, oxygen- or sulfur-containing bonds at almost diffusion-controlled reaction rates.[4,11] Despite the promise of photoactivatable 3H-diazirines as photolabeling agents, the cumbersome synthesis, the instability to ambient light conditions, and the limited aqueous solubility represent major drawbacks for PAL. This Example demonstrates the design, synthesis and evaluation of 3-pyridyl- and 3-pyrimidyl-substituted 3-trifluoromethyl-diazirines 1 and 2 (FIG. 1) as photoaffinity labels displaying favorable ambient light stability without compromising the photoactivated insertion reactivity.

Figure 2A:
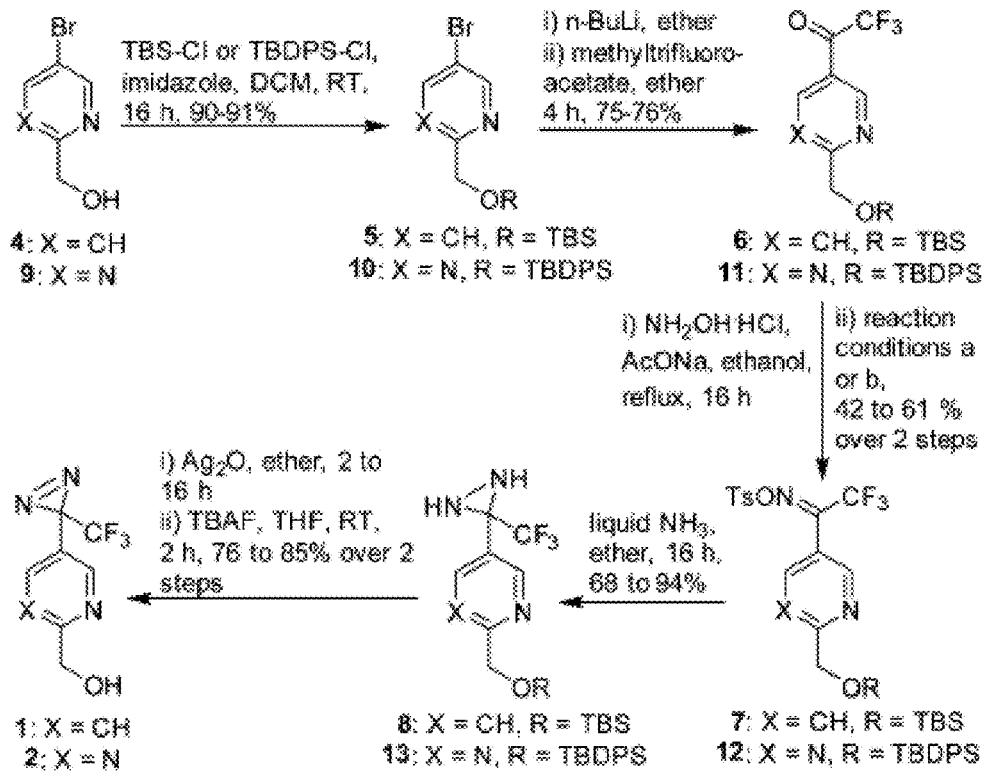
FIGS. 2A-2B shows schemes (FIG. 2A) synthesis of pyridine and pyrimidine 3-trifluoromethyl-3-aryldiazirines 1 and 2 and (FIG. 2B) photoactivation reaction of diazirine photoprobes.

Ambient light conditions commonly promote the spontaneous decomposition of the 3H-diazirines due to ring strain energy of the three-membered diazirine ring. As demonstrated in this Example, the ambient light mediated 3H-diazirine's decay was minimized through electron withdrawing groups while retaining the ability to rapidly react with UV light ($\lambda_{ext}$=320-400 nm) to the corresponding carbene intermediate.[12] As the trifluoromethyl substituent of 3-trifluoromethyl-3-phenyl-diazirine is a very strong electron withdrawing group,[13] Prior studies have shown that aromatic diazirines photochemically produce higher ratios of carbene over the rearranged diazo byproduct compared to aliphatic diazirines,[1, 14, 15] The phenyl group was replaced with an electron withdrawing pyridine or pyrimidine ring in the compounds provided herein. Furthermore, as demonstrated herein the use of a pyridyl- or pyrimidyl-substituent increased the insertion reactivity of the photoactivated intermediate as pyridyl carbenes have been shown to be more reactive than corresponding phenyl analogues.[16] This Example describes and demonstrates generation of pyridine and pyrimidine photolabels 1 and 2 starting from the alcohols 4 and 9[17] (FIG. 2A). For comparative studies, the conventional Brunner-type 3-trifluoromethyl-3-phenyl-diazirine 3 was prepared as previously reported.[14, 18]

Materials and Methods

Experimental Procedures for Synthesis and Biochemical Experiments

General Information.

Commercially available reagents and solvents were used without further purification. All the reactions were done under anhydrous condition and argon atmosphere, unless specified otherwise. Room temperature (RT) experiments were done at 21° C. and overnight experiments were done for 16 hours. Thin layer chromatography (TLC) was performed using EMD silica gel 60-F plates (it is individually specified in instances where neutral alumina TLC plate was used instead) and spots were visualized using UV light or phosphomolybdic acid (PMA) staining solution. Purification by flash chromatography was done using EMD silica gel (230-400 mesh) (it is individually specified in instances where neutral alumina was used instead). NMR experiments were done on a Bruker DPX-250 ($^1$H at 250 MHz and $^{13}$C at 63 MHz), a Varian Inova 400 MHz spectrometer ($^1$H at 400 MHz, $^{13}$C at 100 MHz, and $^{19}$F at 376 MHz), an Inova 500 MHz spectrometer ($^1$H at 500 MHz and $^{13}$C at 125 MHz) or an Inova 600 MHz spectrometer ($^1$H at 600 MHz and $^{13}$C at 150 MHz) and the data was processed using MestReNova. Chemical shifts (δ) are reported in parts per million (ppm) with the solvent peak as the internal standard for $^1$H and $^{13}$C, while trifluorotoluene was used as external standard for $^{19}$F NMR spectroscopy. Coupling constants are reported in Hz. Signals are quoted as s (singlet), d (doublet), t (triplet), q (quartet), m (multiplet), br (broad), dd (doublet of doublets), ddd (doublet of doublets of doublets) or dt (doublet of triplets). High resolution mass spectrometry was performed on Agilent 6540 Ultra-High-Definition (UHD) Q-TOF LC-MS with electrospray ionization. Preparative HPLC was conducted using Agilent Eclipse XDB-C18 PN 990967-202 column with gradient 10% to 50% of acetonitrile in water with 0.05% TFA over 15 min followed by 100% acetonitrile for 5 min (flow rate: 5 ml min$^{-1}$). Agilent 1100 series LC/MSD was used for the solubility measurement experiments. Orel Instruments housing with an Osram 150 W XBO xenon short-arc lamp, fitted with a Schott WG-320 filter to eliminate UV lights below 320 nm, was used for the photoactivation studies. For Western blot analysis anti-biotin-peroxidase antibody produced in goat purchased from Sigma (A4541) was used to detect the biotin labeled proteins. The photographic films (Thermo scientific #34091) used for recording the chemiluminescence in Western blot analysis were developed using Konica Minolta medical film processor (Model SRX-101A). Photolabeled samples were analyzed using a linear ion trap Orbitrap XL (LTQ OrbiTrap XL, Thermo Fisher Corp., Bremen, Germany).

5-bromo-2-(((tert-butyldimethylsilyl)oxy)methyl) pyridine (5)

To a solution of (5-bromopyridin-2-yl)methanol[25] (3.65 g, 19.4 mmol) in anhydrous dichloromethane (DCM) (50 mL), tert-butyldimethylsilyl chloride (3.22 g, 21.3 mmol) and imidazole (2.90 g, 42.6 mmol) were added and stirred overnight at room temperature (RT). The reaction mixture was quenched with saturated ammonium chloride and extracted with dichloromethane (3 times). The combined organic layer was dried with anhydrous sodium sulfate and concentrated. The resultant crude was subjected to flash chromatography with silica column and 10% ethyl acetate in hexanes as eluent to give 5 (5.29 g, 90%) as colorless oil. $R_f$ 0.51 (10% ethyl acetate in hexanes). $^1$H NMR (400 MHz, CDCl$_3$) δ 8.54 (d, J=2.4 Hz, 1H), 7.80 (dd, J=8.4 Hz, J=2.3 Hz, 1H), 7.40 (d, J=8.4 Hz, 1H), 4.76 (s, 2H), 0.94 (s, 9H), 0.10 (s, 6H). $^{13}$C NMR (101 MHz, CDCl$_3$) δ 160.1, 149.7, 139.3, 121.6, 118.6, 65.7, 26.0, 18.4, −5.3. HRMS (ESI$^+$) calcd for C$_{12}$H$_{21}$BrNOSi$^+$ [M+H]$^+$ 302.0570, found: 302.0577.

1-(6-(((tert-butyldimethysily)oxy)methyl)pyridin-3-yl)-2,2,2-trifluoroethanone (6)

To a solution of 5 (4.10 g, 13.6 mmol) in diethyl ether (60 mL) in an argon back flushed flask, n-butyllithium (6.5 mL of 2.5 M solution in hexane) was slowly added at −78° C. and left to stir. After 30 minutes methyl trifluoroacetate (2.09 g, 16.3 mmol) was added and stirred at −78° C. for 2 hours and warmed to room temperature. The reaction was quenched with saturated ammonium chloride and extracted with ethyl acetate (3 times). The combined organic layer was dried with anhydrous sodium sulfate and concentrated. The resultant crude was subjected to flash chromatography with neutral alumina column and 4% methanol in dichloromethane as eluent to give 6 (3.3 g, 76%) as pale yellow oil. $R_f$ 0.45 (6% methanol in dichloromethane, neutral alumina TLC plate). $^1$H NMR (400 MHz, CDCl$_3$) δ 9.14 (s, 1H), 8.35 (d, J=7.8 Hz, 1H), 7.74 (d, J=7.9 Hz, 1H), 4.90 (s, 2H), 0.96 (s, 9H), 0.14 (s, 6H). $^{13}$C NMR (101 MHz, CDCl$_3$) δ 179.8 (q, J=36.6 Hz), 169.0 (s), 150.5 (q, J=2.7 Hz), 138.1 (q, J=1.9 Hz), 124.4 (s), 120.2 (s), 116.5 (q, J=291.0 Hz), 66.07 (s), 26.0 (s), 18.5 (s), −5.3 (s). $^{19}$F NMR (376 MHz, CDCl$_3$) δ −72.30 (s). HRMS (ESI$^+$) calcd for C$_{14}$H$_{21}$F$_3$NO$_2$Si$^+$ [M+H]$^+$ 320.1288, found: 320.1297.

1-(6-(((tert-butyldimethysilyl)oxy)methyl)pyridin-3-yl)-2, 2, 2-trifluoroethanone O-tosyl oxime (7)

A suspension of hydroxylamine hydrochloride (0.36 g, 5.18 mmol) and sodium acetate trihydrate (0.93 g, 6.83 mmol) in ethanol (5 mL) was stirred for 10 minutes and allowed to settle. The supernatant of the above mixture was transferred to a solution of 6 (0.55 g, 1.72 mmol) in ethanol (2 mL) and refluxed for 16 hours. Upon cooling to room temperature ethanol was removed under reduced pressure and the resultant concentrate was extracted between water and dichloromethane (water layer was extracted with dichloromethane 3 times). The combined organic layer was dried with anhydrous sodium sulfate and concentrated. The concentrated crude was back flushed with argon and anhydrous dichloromethane (5 mL) was added followed by pyridine (273 mg, 3.45 mmol) and 4-dimethylaminopyridine (DMAP) (21.0 mg, 0.17 mmol). The solution was cooled to 0° C. and p-toluenesulfonic anhydride (619 mg, 1.90 mmol) was added slowly and stirred at the same temperature for 30 minutes followed by 2 hours at room temperature. The reaction was quenched with water and extracted with dichloromethane (3 times). The combined organic layer was dried with anhydrous sodium sulfate and concentrated. The resultant crude was subjected to flash chromatography with silica column and 10% ethyl acetate in hexanes as eluent to give 7 (0.51 g, 61%) as colorless oil. $R_f$ 0.37 (10% ethyl aceate in hexanes). $^1$H NMR (400 MHz, CDCl$_3$) δ 8.51 (s, 1H), 7.86 (d, J=8.2 Hz, 2H), 7.76 (m, 1H), 7.65 (m, 1H), 7.36 (d, J=8.0 Hz, 2H), 4.84 (s, 2H), 2.44 (s, 3H), 0.94 (s, 9H), 0.12 (s, 6H). $^{13}$C NMR (101 MHz, CDCl$_3$) δ 165.3, 151.8 (q, J=34.3 Hz), 147.9, 146.5, 136.9, 131.1, 130.1, 129.3, 119.8, 119.6 (q, J=277 Hz), 119.4, 65.9, 25.9, 21.8, 18.4, −5.3. $^{19}$F NMR (376 MHz, CDCl$_3$) δ −66.81 (s). HRMS (ESI$^+$) calcd for $C_{21}H_{28}F_3N_2O_4SSi^+$ [M+H]$^+$ 489.1486, found: 489.1497.

2-(((tert-butyldimethylsily)oxy)methyl)-5-(3-(trifluoromethy)diaziridin-3-yl)pyridine (8)

To a solution of 7 (1.28 g, 2.62 mmol) in anhydrous diethyl ether (15 mL) at −50° C., ammonia gas was bubbled and condensed till the volume increased by 15 mL. This solution was stirred vigorously at −50° C. overnight and the ammonia was allowed to evaporate by removing the cold bath. After warming to room temperature the reaction mixture was extracted between water/brine (4:1) and diethyl ether (aqueous layer was extracted with ether 3 times) and the combined organic layer was dried with anhydrous sodium sulfate and concentrated. The concentrated crude was subjected to flash chromatography with silica column and 15% ethyl acetate in hexanes as eluent to give 8 (0.82 g, 94%) as colorless oil. $R_f$ 0.33 (20% ethyl aceate in hexanes). $^1$H NMR (400 MHz, CDCl$_3$) δ 8.65 (s, 1H), 7.89 (d, J=8.2 Hz, 1H), 7.53 (d, J=8.2 Hz, 1H), 4.79 (s, 2H), 2.89 (d, J=8.7 Hz, 1H), 2.43 (d, J=8.7 Hz, 1H), 0.92 (s, 9H), 0.09 (s, 6H). $^{13}$C NMR (101 MHz, CDCl$_3$) δ 163.6, 148.3, 136.7, 126.0, 123.4 (q, J=278 Hz), 119.7, 65.8, 56.6 (q, J=36.7 Hz), 25.9, 18.4, −5.38. $^{19}$F NMR (376 MHz, CDCl$_3$) δ −75.73 (s). HRMS (ESI$^+$) calcd for $C_{14}H_{23}F_3N_3OSi^+$ [M+H]$^+$ 334.1557, found: 334.1568.

(5-(3-(trifluoromethyl)-3H-diazirin-3-yl)pyridin-2-yl)methanol (1)

To a solution of 8 (0.13 g, 0.390 mmol) in anhydrous diethyl ether (4.0 mL), freshly prepared Ag$_2$O (prepared by dropwise addition of a 10% aqueous solution of sodium hydroxide to a 10% solution of silver nitrate under constant stirring and the resultant black residue was filtered, washed with deionized water and oven dried for 2 hours) (0.45 g, 1.94 mmol) was added and stirred overnight at room temperature. The reaction was filtered and the filtrate was concentrated, to it THF (2 mL) was added and redissolved. This solution was cooled to 0° C. and a 1M solution of tetrabutylammonium fluoride (TBAF) in THF (0.47 mL, 0.470 mmol) was added drop wise and stirred till the completion of reaction as indicated by TLC (about 1 hour). The reaction was extracted between water/brine (1:1) and ethyl acetate (aqueous layer was extracted with ethyl acetate 3 times) and the combined organic layer was dried with anhydrous sodium sulfate and concentrated. The resultant crude was purified by flash column chromatography with silica column and 20% ethyl acetate in hexanes as eluent to give 1 (64.4 mg, 76%) as colorless oil. $R_f$ 0.46 (50% ethyl acetate in hexanes). $^1$H NMR (400 MHz, CDCl$_3$) δ 8.43 (s, 1H), 7.56 (d, J=8.2 Hz, 1H), 7.34 (d, J=8.3 Hz, 1H), 4.79 (s, 2H), 3.63 (s, 1H). $^{13}$C NMR (101 MHz, CDCl$_3$) δ 161.5, 146.9, 135.2, 124.1, 121.8 (q, J=275 Hz), 120.5, 64.2, 27.1 (q, J=41.6 Hz). $^{19}$F NMR (376 MHz, CDCl$_3$) δ −65.68 (s). HRMS (ESI$^+$) calcd for $C_8H_7F_3N_3O^+$ [M+H]$^+$ 218.0536, found: 218.0537.

5-bromo-2-(((tert-butyldiphenylsilyl)oxy)methyl) pyrimidine (10)

To a solution of (5-bromopyrimidin-2-yl)methanol[26] (5.93 g, 31.4 mmol) in anhydrous dichloromethane (DCM) (90 mL), tert-butyldiphenylsilyl chloride (10.3 g, 37.6 mmol) and imidazole (5.13 g, 75.3 mmol) were added and stirred overnight at room temperature. The reaction mixture was quenched with saturated ammonium chloride and extracted with dichloromethane (the aqueous layer was extracted with dichloromethane 3 times). The combined organic layers were dried with anhydrous sodium sulfate and concentrated. The resultant crude was subjected to flash chromatography with silica column and 3% ethyl acetate in hexanes as eluent to give 10 (12.2 g, 91%) as colorless oil. $R_f$ 0.60 (10% ethyl acetate in hexanes). $^1$H NMR (400 MHz, CDCl$_3$) δ 8.74 (s, 2H), 7.76-7.69 (m, 4H), 7.45-7.32 (m, 6H), 4.89 (s, 2H), 1.10 (s, 9H). $^{13}$C NMR (101 MHz, CDCl$_3$) δ 167.0, 157.8, 135.8, 133.4, 129.9, 127.8, 118.7, 67.1, 26.9, 19.5. HRMS (ESI$^+$) calcd for $C_{15}H_{18}BrN_2OSi^+$ [M-C$_6$H$_5^−$]$^+$ 349.0366, found: 349.0374.

1-(2-(((tert-butyldiphenylsilyl)oxy)methyl)pyrimidin-5-yl)-2,2,2-trifluoroethanone (11)

A solution of 10 (10.0 g, 23.4 mmol) and tetramethylethylenediamine (TMEDA) (3.53 g, 30.4 mmol) in anhydrous THF (195 mL) in an argon back flushed flask was cooled to −110° C. (ethanol and liquid N$_2$ bath). To this cold solution n-butyllithium (9.9 mL of 2.5 M solution in hexanes) was added very slowly under constant stirring. After 3 minutes (any longer would result in undesired side products), methyl trifluoroacetate (5.99 g, 46.8 mmol) was added dropwise and stirred at −110° C. for 30 minutes and slowly warmed to RT. The reaction was quenched with saturated aqueous ammonium chloride solution and extracted with ethyl acetate (the aqueous layer was extracted with ethyl acetate 3 times). The combined organic layer was dried with anhydrous sodium sulfate and concentrated. The resultant crude was subjected to flash chromatography with neutral alumina column and 5% methanol in dichloromethane as eluent to give 11 (7.81 g, 75%) as pale yellow liquid. $R_f$ 0.49 (5% methanol in dichloromethane, neutral alumina TLC plate). HRMS (ESI$^+$) calcd for $C_{23}H_{26}F_3N_2O_3Si^+$ [M+H$_3$O]$^+$ (since 11 exists as geminal diol) 463.1659, found: 463.1664.

1-(2-(((tert-butyldiphenylsilyl)oxy)methyl)pyrimidin-5-yl)-2,2,2-trifluoroethanone O-tosyl oxime (12)

A suspension of hydroxylamine hydrochloride (7.04 g, 101 mmol) and sodium acetate trihydrate (23.6 g, 173 mmol) in ethanol (128 mL) was stirred vigorously for 10 minutes and allowed to settle. The clear supernatant (100 mL) of the above mixture was transferred to a flask with 11 (6.44 g, 14.5 mmol) and refluxed for 40 hours. Upon cooling to room temperature ethanol was removed under reduced pressure and the resultant residue was extracted between water and dichloromethane (the aqueous layer was extracted with dichloromethane 3 times) and the combined organic layer was dried with anhydrous sodium sulfate and concentrated. The concentrated crude was back flushed with argon and anhydrous dichloromethane (48 mL) was added, followed by 4-dimethylaminopyridine (DMAP) (178 mg, 1.45 mmol). After cooling the solution to −50° C., N,N-Diisopropylethylamine (DIPEA) (2.06 g, 15.9 mmol) was added followed by part-wise addition of p-toluenesulfonyl chloride (3.03 g, 15.9 mmol) and the reaction temperature was increased slowly in such a way that it reached 0° C. in 2 hours. The reaction was quenched with water and extracted with dichloromethane (the aqueous layer was extracted with dichloromethane 3 times). The combined organic layer was dried with anhydrous sodium sulfate and concentrated. The resultant crude was subjected to flash column chromatography with silica column and 10% ethyl acetate in hexanes as eluent to give 12 (3.73 g, 42%) as pale yellow oil. $R_f$ 0.38 (10% ethyl aceate in hexanes). $^1$H NMR (400 MHz, CDCl$_3$) δ 8.77 (s, 2H), 7.91 (d, J=8.3 Hz, 2H), 7.74 (dd, J=7.9, 1.4 Hz, 4H), 7.45-7.36 (m, 8H), 5.02 (s, 2H), 2.49 (s, 3H), 1.14 (s, 9H). $^{13}$C NMR (101 MHz, CDCl$_3$) δ 171.5, 156.4, 149.2 (q, J=35.1 Hz), 146.8, 135.8, 133.2, 130.8, 130.2, 129.9, 129.5, 127.9, 119.4 (q, J=277 Hz), 118.1, 67.2, 26.9, 21.9, 19.5. $^{19}$F NMR (376 MHz, CDCl$_3$) δ −66.69 (s). HRMS (ESI$^+$) calcd for C$_{30}$H$_{30}$F$_3$N$_3$NaO$_4$SSi$^+$ [M+Na]$^+$ 636.1571, found: 636.1587.

2-(((tert-butyldiphenylsilyl)oxy)methyl)-5-(3-(trifluoromethyl)diaziridin-3-yl)pyrimidine (13)

A solution of 12 (1.74 g, 2.83 mmol) in anhydrous diethyl ether (15 mL) was cooled to −50° C. and ammonia gas was bubbled and condensed till the volume increased by 15 mL. This solution was stirred vigorously at −50° C. overnight and the ammonia was allowed to evaporate by removing the cold bath. After warming to RT the reaction mixture was extracted between water/brine (4:1) and diethyl ether (the aqueous layer was extracted with ether 3 times) and the combined organic layer was dried with anhydrous sodium sulfate and concentrated. The concentrated crude was subjected to flash chromatography with silica column and 15% ethyl acetate in hexanes as eluent to give 13 (881 mg, 68%) as colorless oil. $R_f$ 0.31 (20% ethyl aceate in hexanes). $^1$H NMR (600 MHz, CDCl$_3$) δ 8.92 (s, 2H), 7.74 (m, 4H), 7.43-7.39 (m, 2H), 7.38-7.34 (m, 4H), 4.99 (s, 2H), 2.92 (d, J=8.8 Hz, 1H), 2.30 (d, J=8.8 Hz, 1H), 1.12 (s, 9H). $^{13}$C NMR (151 MHz, CDCl$_3$) b 170.4, 156.9, 135.8, 133.3, 129.9, 127.8, 124.2, 123.0 (q, J=278 Hz), 67.3, 55.2 (q, J=37.5 Hz), 26.9, 19.5. $^{19}$F NMR (376 MHz, CDCl$_3$) δ −75.5 (s). HRMS (ESI$^+$) calcd for C$_{23}$H$_{26}$F$_3$N$_4$OSi$^+$ [M+H]$^+$ 459.1822, found: 459.1833.

(5-(3-(trifluoromethyl)-3H-diazirin-3-yl)pyrimidin-2-yl) methanol (2)

To a solution of 13 (790 mg, 1.72 mmol) in anhydrous diethyl ether (20 mL), freshly prepared Ag$_2$O (prepared by dropwise addition of a 10% aqueous solution of sodium hydroxide to a 10% solution of silver nitrate under constant stirring and the resultant black residue was filtered, washed with deionized water and oven dried for 2 hours) (1.90 g, 8.20 mmol) was added and stirred overnight at room temperature. The reaction was filtered and the filtrate was concentrated under reduced pressure. To the resultant concentrate THF (7 mL) was added and redissolved. To it a 1M solution of tetrabutylammonium fluoride (TBAF) in THF (1.9 mL) was added drop wise at 0° C. and stirred for 30 minutes. The reaction was extracted between brine and ethyl acetate (the aqueous layer was extracted with ethyl acetate 2 times) and the combined organic layer was dried with anhydrous sodium sulfate and concentrated. The resultant crude was purified by flash column chromatography with silica column and 25% ethyl acetate in hexanes as eluent to give 2 (317 mg, 85%) as colorless oil. $R_f$ 0.48 (50% ethyl acetate in hexanes). $^1$H NMR (400 MHz, CD$_3$OD) δ 8.76 (s, 2H), 4.80 (s, 2H). $^{13}$C NMR (101 MHz, CD$_3$OD) δ 170.3, 155.8, 121.6, 121.5 (q, J=274 Hz), 64.2, 25.5 (q, J=42.5 Hz). $^{19}$F NMR (376 MHz, CD$_3$OD) δ −67.8 (s). HRMS (ESI$^+$) calcd for C$_7$H$_6$F$_3$N$_4$O [M+H]$^+$ 219.0488, found: 219.0495.

(S)-4-(3-(trifluoromethyl)-3H-diazirin-3-yl)benzyl 2-acetamido-3-(1H-indol-3-yl)propanoate (14)

To a solution of (4-(3-(trifluoromethyl)-3H-diazirin-3-yl)phenyl)methanol (30.0 mg, 139 μmol) in anhydrous dimethylformamide (DMF) (0.9 mL), N-acetyl tryptophan (51.3 mg, 208 μmol), EDC (41.0 mg, 214 μmol) and DMAP (26.0 mg, 213 μmol) were added at room temperature and stirred for 2 hours. The reaction was quenched with the addition of water (3 mL) and extracted with diethyl ether (the aqueous layer was extracted with ether 3 times). The combined organic layer was dried with anhydrous sodium sulfate and concentrated. The resultant crude compound was purified by silica flash column chromatography with 50% ethyl acetate in hexanes as eluent to yield 14 (41.0 mg, 66%) as colorless oil. $R_f$ 0.23 (50% ethyl acetate in hexanes). $^1$H NMR (400 MHz, CDCl$_3$) δ 8.33 (s, 1H), 7.51 (d, J=7.9 Hz, 1H), 7.35 (d, J=8.1 Hz, 1H), 7.22-7.16 (m, 3H), 7.16-7.07 (m, 3H), 6.82 (d, J=2.1 Hz, 1H), 6.09 (d, J=7.8 Hz, 1H), 5.06 (s, 2H), 4.99 (dt, J=7.8, 5.6 Hz, 1H), 3.30 (d, J=5.6 Hz, 2H), 1.95 (s, 3H). $^{13}$C NMR (101 MHz, CDCl$_3$) δ 171.9, 170.0, 137.0, 136.3, 129.2, 128.6, 127.7, 126.8, 122.9, 122.4, 122.2 (q, J=275 Hz), 119.8, 118.5, 111.5, 109.8, 66.3, 53.3, 28.4 (q, J=40.4 Hz), 27.8, 23.3. $^{19}$F NMR (376 MHz, CDCl$_3$) δ −65.22 (s). HRMS (ESI$^+$) calcd for C$_{22}$H$_{20}$F$_3$N$_4$O$_3$$^+$ [M+H]$^+$ 445.1482, found: 445.1480.

(S)-(5-(3-(trifluoromethyl)-3H-diazirin-3-yl)pyridin-2-yl)methyl 2-acetamido-3-(1H-indol-3-yl)propanoate (15)

To a solution of 1 (24.0 mg, 111 μmol) in anhydrous DMF (0.7 mL) N-acetyl tryptophan (41.0 mg, 166 μmol), EDC (30.0 mg, 156 μmol) and DMAP (19.0 mg, 156 μmol) were added at room temperature and stirred for 16 hours. The reaction was quenched with the addition of water (2 mL) and extracted with diethyl ether (the aqueous layer was extracted with ether 3 times). The combined organic layer was dried with anhydrous sodium sulfate and concentrated. The resultant crude compound was purified by silica flash column chromatography with 60% ethyl acetate in hexanes as eluent to yield 15 (38.2 mg, 77%) as white solid. $R_f$ 0.37 (70% ethyl acetate in hexanes). mp 115-117° C. $^1$H NMR (400 MHz, CDCl$_3$) δ 8.49 (s, 1H), 8.39 (s, 1H), 7.53 (d, J=7.9 Hz, 1H), 7.42 (dd, J=8.3, 2.3 Hz, 1H), 7.33 (d, J=8.1 Hz, 1H), 7.20-7.15 (m, 1H), 7.12-7.04 (m, 2H), 6.98 (d, J=2.3 Hz, 1H), 6.19 (d, J=7.6 Hz, 1H), 5.19 (q, J=14.0 Hz, 2H), 5.03 (dt, J=7.6, 5.9 Hz, 1H), 3.33 (d, J=5.9 Hz, 2H), 1.96 (s, 3H). $^{13}$C NMR (101 MHz, CDCl$_3$) δ 171.8, 170.2, 156.8, 147.2, 136.3, 135.4, 127.7, 124.7, 123.0, 122.4, 121.8 (q, J=275 Hz), 121.2, 119.9, 118.5, 111.5, 109.8, 66.7, 53.4, 27.8, 27.1 (q, J=41.8 Hz), 23.2. $^{19}$F NMR (376 MHz, CDCl$_3$) δ −65.52 (s). HRMS (ESI$^+$) calcd for C$_{21}$H$_{19}$F$_3$N$_5$O$_3^+$ [M+H]$^+$ 446.1435, found: 446.1446.

(S)-(5-(3-(trifluoromethyl)-3H-diazirin-3-yl)pyrimidin-2-yl)methyl 2-acetamido-3-(1H-indol-3-yl)propanoate (16)

To a solution of 2 (22.0 mg, 101 μmol) in anhydrous DMF (0.7 mL) N-acetyl tryptophan (38.0 mg, 154 μmol), EDC (30.0 mg, 156 μmol) and DMAP (19.0 mg, 156 μmol) were added at room temperature and stirred for 4 hours. The reaction was quenched with the addition of water (2 mL) and extracted with diethyl ether (the aqueous layer was extracted with ether 3 times). The combined organic layer was dried with anhydrous sodium sulfate and concentrated. The resultant crude compound was purified by silica flash column chromatography with 70% ethyl acetate in hexanes as eluent to yield 16 (28.0 mg, 62%) as white solid. R$_f$ 0.26 (70% ethyl acetate in hexanes). mp 94-96° C. $^1$H NMR (400 MHz, CDCl$_3$) δ 8.53 (s, 2H), 8.46 (s, 1H), 7.55 (d, J=7.9 Hz, 1H), 7.34 (d, J=8.1 Hz, 1H), 7.17 (t, J=7.6 Hz, 1H), 7.12-7.05 (m, 2H), 6.15 (d, J=7.8 Hz, 1H), 5.41-5.30 (m, 2H), 5.12 (dd, J=7.7, 5.5 Hz, 1H), 3.48-3.33 (m, 2H), 1.93 (s, 3H). $^{13}$C NMR (101 MHz, CDCl$_3$) δ 171.8, 170.1, 165.6, 155.7, 136.2, 127.9, 123.2, 122.6, 122.3, 121.4 (q, J=275 Hz), 119.8, 118.6, 111.4, 110.0, 66.0, 53.2, 27.5, 25.9 (q, J=42.7 Hz), 23.3. $^{19}$F NMR (376 MHz, CDCl$_3$) δ −65.67 (s). HRMS (ESI$^+$) calcd for C$_{20}$H$_{18}$F$_3$N$_6$O$_3^+$ [M+H]$^+$ 447.1387, found: 447.1383.

4-((4-(3-(trifluoromethyl)-3H-diazirin-3-yl)benzyl)oxy)quinoline (17)

To a solution of (4-(3-(trifluoromethyl)-3H-diazirin-3-yl)phenyl)methanol (35.4 mg, 164 μmol) in anhydrous dichloromethane (2.5 mL), phosphorous tribromide (51.0 mg, 188 μmol) was added dropwise at 0° C. and warmed to room temperature. After stirring for 8 hours the reaction was quenched with the addition of brine solution (0.5 ml) and followed by the dropwise addition of saturated sodium bicarbonate solution till the bubbling stops. The dichloromethane layer was separated and further extraction of the aqueous layer was done with fresh dichloromethane (2 more times). The combined dichloromethane layer was dried with anhydrous sodium sulfate and concentrated, high vacuum should be avoided during concentration due to the volatile nature of the product. To the resultant concentrate dichloromethane (2.5 mL), water (2.5 mL), 4-quinolinol (71.0 mg, 489 μmol), tetra-n-butylammonium bromide (53.0 mg, 164 μmol) and sodium hydroxide (20.0 mg, 500 μmol) were added at room temperature and stirred for 16 hours. The dichloromethane layer was isolated and the water layer was extracted 2 more times with fresh dichloromethane. The combined dichloromethane layer was dried with anhydrous sodium sulfate and concentrated. The resultant crude compound was purified by silica flash column chromatography with 80% ethyl acetate in hexanes as eluent to yield 17 as white solid (43.2 mg, 77%). mp 123-125° C. $^1$H NMR (400 MHz, CDCl$_3$) δ 8.44 (d, J=7.9 Hz, 1H), 7.63 (d, J=7.6 Hz, 1H), 7.52 (t, J=7.6 Hz, 1H), 7.33 (t, J=7.5 Hz, 1H), 7.22-7.11 (m, 5H), 6.33 (d, J=7.7 Hz, 1H), 5.34 (s, 2H). $^{13}$C NMR (101 MHz, CDCl$_3$) δ 178.3, 143.7, 140.0, 137.1, 132.5, 129.4, 127.5, 127.2, 126.6, 124.1, 120.7, 116.0, 110.7, 56.0. $^{19}$F NMR (376 MHz, CDCl$_3$) δ −65.23 (s). HRMS (ESI$^+$) calcd for C$_{18}$H$_{13}$F$_3$N$_3$O$^+$ [M+H]$^+$ 344.1005, found: 344.1014.

4-((5-(3-(trifluoromethyl)-3H-diazirin-3-yl)pyridin-2-yl)methoxy)quinoline (18)

To a solution of 1 (23.0 mg, 106 μmol) in anhydrous dichloromethane (1.5 mL), phosphorous tribromide (33.0 mg, 122 μmol) was added dropwise at 0° C. and warmed to room temperature. After stirring for 10 hours the reaction was quenched with the addition of brine solution (0.5 ml) and followed by the dropwise addition of saturated sodium bicarbonate solution till the bubbling stops. The dichloromethane layer was separated and further extraction of the aqueous layer was done with fresh dichloromethane (2 more times). The combined dichloromethane layer was dried with anhydrous sodium sulfate and concentrated, high vacuum should be avoided during concentration due to the volatile nature of the product. To the resultant concentrate dichloromethane (1.5 mL), water (1.5 mL), 4-quinolinol (46.0 mg, 317 μmol), tetra-n-butylammonium bromide (34.0 mg, 105 μmol) and sodium hydroxide (13.0 mg, 325 μmol) were added at room temperature and stirred for 3 hours. The dichloromethane layer was isolated and the water layer was extracted 2 more times with fresh dichloromethane. The combined dichloromethane layer was dried with anhydrous sodium sulfate and concentrated. The resultant crude compound was purified by silica flash column chromatography with 2% methanol in dichloromethane as eluent to yield 18 as white solid (18.1 mg, 50%). R$_f$ 0.39 (5% methanol in dichloromethane). mp 123-125. $^1$H NMR (400 MHz, CDCl$_3$) δ 8.46-8.40 (m, 2H), 7.71 (d, J=7.7 Hz, 1H), 7.52 (ddd, J=8.7, 7.1, 1.6 Hz, 1H), 7.44 (dd, J=8.3, 2.3 Hz, 1H), 7.33 (t, J=7.6 Hz, 1H), 7.22 (d, J=8.7 Hz, 1H), 7.02 (d, J=8.3 Hz, 1H), 6.37 (d, J=7.7 Hz, 1H), 5.42 (s, 2H). $^{13}$C NMR (101 MHz, CDCl$_3$) δ 178.2, 156.8, 148.2, 144.1, 140.0, 135.7, 132.7, 127.3, 125.2, 124.2, 121.7 (q, J=275 Hz), 120.6, 115.9, 110.8, 57.9, 27.1 (q, J=41.8 Hz). $^{19}$F NMR (376 MHz, CDCl$_3$) δ −65.49 (s). HRMS (ESI$^+$) calcd for C$_{17}$H$_{12}$F$_3$N$_4$O$^+$ [M+H]$^+$ 345.0958, found: 345.0966.

4-((5-(3-(trifluoromethyl)-3H-diazirin-3-yl)pyrimidin-2-yl)methoxy)quinoline (19)

To a solution of 2 (23.0 mg, 105 μmol) in anhydrous dichloromethane (1.5 mL), phosphorous tribromide (33.0 mg, 122 μmol) was added dropwise at 0° C. and warmed to room temperature. After stirring for 10 hours the reaction was quenched with the addition of brine solution (0.5 ml) and followed by the dropwise addition of saturated sodium bicarbonate solution till the bubbling stops. The dichloromethane layer was separated and further extraction of the aqueous layer was done with fresh dichloromethane (2 more times). The combined dichloromethane layer was dried with anhydrous sodium sulfate and concentrated, high vacuum should be avoided during concentration due to the volatile nature of the product. A solution of 4-quinolinol (60.0 mg, 413 μmol) and potassium carbonate (36.0 mg, 261 μmol) in water (1.5 mL) was stirred for 10 minutes and filtered through 0.45 μm syringe filter. This aqueous solution was added to the crude concentrate of the bromide intermediate in dichloromethane (1.5 mL) and followed by the addition of tetra-n-butylammonium bromide (34.0 mg, 105 μmol) at room temperature and stirred for 2 hours. The dichloromethane layer was isolated and the water layer was extracted 2 more times with fresh dichloromethane. The combined dichloromethane layer was dried with anhydrous sodium sulfate and concentrated. The resultant crude compound was purified by silica flash column chromatography with 2% methanol in dichloromethane as eluent to yield 19 as white solid (24.5 mg, 68%). $R_f$ 0.37 (5% methanol in dichloromethane). mp 115-117° C. $^1$H NMR (400 MHz, CDCl$_3$ with 3% CD$_3$OD) δ 8.54 (s, 2H), 8.40-8.35 (m, 1H), 7.76 (d, J=7.7 Hz, 1H), 7.53 (ddd, J=8.7, 7.2, 1.5 Hz, 1H), 7.35-7.29 (m, 2H), 6.33 (d, J=7.7 Hz, 1H), 5.48 (s, 2H). $^{13}$C NMR (101 MHz, CDCl$_3$ with 3% CD$_3$OD) δ 178.9, 165.4, 156.1, 144.8, 140.2, 132.6, 127.1, 127.0, 124.1, 123.2, 121.3 (q, J=275 Hz), 115.7, 110.3, 58.1, 25.8 (q, J=42.8 Hz). $^{19}$F NMR (376 MHz, CDCl$_3$ with 3% CD$_3$OD) δ −65.67 (s). HRMS (ESI$^+$) calcd for C$_{16}$H$_{11}$F$_3$N$_5$O$^+$ [M+H]$^+$ 346.0910, found: 346.0918.

N-(6-aminohexyl)-5-((4S)-2-oxohexahydro-1H-thieno[3, 4-d]imidazol-4-yl)pentanamide (23)

The trifluoroacetic acid salt of amine 23 was synthesized as outlined by Kottani and co-workers.[24] The free base of 23 was prepared by using the following procedure using Amberlite IRA-402 (OH$^-$ form) (Amberlite IRA-402 was freshly activated by stirring the resin in 10% NaOH aqueous solution for 10 minutes, followed by filtration and washing the resin with deionized water). After the BOC deprotection the excess trifluroacetic acid (TFA) and dichloromethane were removed in the rotavap followed by high vacuum for 6 hours with slow stirring. The resulting TFA salt residue of 23 was redissolved in water (2 mL per 100 mg of residue) and to this solution freshly activated Amberlite IRA-402 (OH$^-$ form) was added in small portions with vigorous stirring. The addition of Amberlite IRA-402 was continued till the pH of the solution was found to be slightly basic as indicated by pH paper. The resin was filtered off and the water layer was freeze dried to get 23 as a free base. $^1$H NMR (400 MHz, CD$_3$OD) δ 4.49 (ddd, J=7.9, 5.0, 0.9 Hz, 1H), 4.30 (dd, J=7.9, 4.5 Hz, 1H), 3.28-3.07 (m, 4H), 2.98-2.83 (m, 1H), 2.76-2.54 (m, 3H), 2.19 (t, J=7.4 Hz, 2H), 1.83-1.23 (m, 15H). $^{13}$C NMR (101 MHz, CD$_3$OD) δ 176.0, 166.1, 63.4, 61.6, 57.0, 41.70, 41.0, 40.2, 36.8, 31.5, 30.3, 29.8, 29.5, 27.6, 27.4, 26.9. HRMS (ESI$^+$) calcd for C$_{16}$H$_{31}$N$_4$O$_2$S$^+$ [M+H]$^+$ 343.2162, found: 343.2164.

(2R,3R,4S,5S,6S)-2-(acetoxymethyl)-6-(2-(benzyloxy)-2-oxoethoxy)tetrahydro-2H-pyran-3,4,5-triyl triacetate (28)

To a solution of mannose pentaacetate (0.50 g, 1.28 mmol) and benzyl 2-hydroxyacetate (425 mg, 2.56 mmol) in anhydrous dichloromethane (7 mL) at 0° C., boron trifluoride etherate (0.8 mL) was added slowly and let to stir overnight at room temperature. The reaction was quenched by the drop wise addition of aqueous saturated sodium bicarbonate solution and extracted between dichloromethane and aqueous saturated sodium bicarbonate solution (the aqueous layer was extracted with dichloromethane 3 times). The combine organic layer was dried with anhydrous sodium sulfate and concentrated under reduced pressure. The concentrated crude was subjected to flash chromatography with silica column and 30% ethyl acetate in hexanes as eluent to give 28 (0.433 g, 68%) as colorless gum. $R_f$ 0.56 (50% ethyl aceate in hexanes). $^1$H NMR (600 MHz, CDCl$_3$) δ 7.31-7.23 (m, 5H), 5.32-5.27 (m, 2H), 5.26-5.20 (m, 1H), 5.11 (d, J=3.0 Hz, 2H), 4.88 (d, J=1.4 Hz, 1H), 4.24 (d, J=16.5 Hz, 1H), 4.17 (dd, J=12.3, 5.0 Hz, 1H), 4.13 (d, J=16.4 Hz, 1H), 4.10-4.05 (m, 1H), 3.97 (dd, J=12.3, 2.4 Hz, 1H), 2.07 (s, 3H), 2.00 (s, 3H), 1.96 (s, 3H), 1.91 (s, 3H). $^{13}$C NMR (63 MHz, CDCl$_3$) δ 170.3, 169.5, 169.5, 168.7, 135.0, 128.4, 128.3, 128.2, 97.7, 68.9, 68.7, 66.6, 65.6, 64.4, 62.0, 20.5, 20.4, 20.4, 20.4. HRMS (ESI$^+$) calcd for C$_{23}$H$_{32}$NO$_{12}$$^+$ [M+NH$_4$]$^+$ 514.1919, found: 514.1930.

2-(((2S,3S,4S,5R,6R)-3, 4, 5-triacetoxy-6-(acetoxymethyl)tetrahydro-2H-pyran-2-yl)oxy)acetic acid (24)

To a solution of 28 (1.22 g, 2.46 mmol) in ethyl acetate (8 mL), palladium (10%) on carbon (0.25 g) was added and subjected to hydrogenation at 60 psi for 18 hours in a hydrogenator. After the reaction was complete as indicated by LC-MS, it was filtered using a syringe filter and the resultant filtrate was concentrated and subjected to preparative HPLC using reverse phase separation to yield the desired 24 (0.70 g, 70%) as colorless gum. 1H NMR (600 MHz, CD$_3$OD) δ 5.35 (dd, J=3.4, 1.7 Hz, 1H), 5.32 (dd, J=10.1, 3.4 Hz, 1H), 5.28-5.23 m, 1H), 4.95 (d, J=1.7 Hz, 1H), 4.31-4.27 (m, 1H), 4.26-4.21 (m, 2H), 4.20-4.17 (m, 1H), 4.13-4.09 (m, 1H), 2.14 (s, 3H), 2.06 (s, 3H), 2.04 (s, 3H), 1.96 (s, 3H). $^{13}$C NMR (63 MHz, CD$_3$OD) δ 172.8, 172.4, 171.6, 171.5, 99.2, 70.7, 70.5, 70.4, 67.1, 65.3, 63.5, 20.7, 20.64, 20.6. HRMS (ESI$^+$) calcd for C$_{16}$H$_{26}$NO$_{12}$$^+$ [M+NH$_4$]$^+$ 424.1450, found: 424.1450.

3-(4-(bromomethyl)phenyl)-3-(trifluoromethyl)-3H-diazirine (25)

To a solution of (4-(3-(trifluoromethyl)-3H-diazirin-3-yl) phenyl)methanol (95.0 mg, 0.439 mmol) in anhydrous dichloromethane (1.5 mL), triphenylphosphine (134 mg, 0.51 mmol) and carbon tetrabromide (168 mg, 0.51 mmol) were added at room temperature and stirred overnight. The reaction was quenched with the addition of pentane and filtered. The filtrate was concentrated, the resultant crude was subjected to flash chromatography with silica column and 5% ether in pentane was used as eluent. The pure fractions as identified by TLC were combined and concentrated. Due to the volatile nature of the product only mild vacuum should be employed to remove the solvents to yield 25 (112 mg, 91%) as colorless liquid. $R_f$=0.61 (10% ethyl aceate in hexanes). $^1$H NMR (400 MHz, CD$_2$Cl$_2$) δ 7.45 (d, J=8.3 Hz, 2H), 7.20 (d, J=8.3 Hz, 2H), 4.50 (s, 2H). $^{13}$C NMR (101 MHz, CD$_2$Cl$_2$) δ 139.7, 129.4, 129.0, 126.8 (q, J=1.3 Hz), 122.0 (q, J=275 Hz), 32.1, 28.2 (q, J=40.4 Hz). $^{19}$F NMR (376 MHz, CD$_2$Cl$_2$) δ −65.67 (s).

2-(bromomethyl)-5-(3-(trifluoromethyl)-3H-diazirin-3-yl)pyridine (26)

To a solution of 1 (59.0 mg, 272 μmol) in anhydrous dichloromethane (0.8 mL), triphenylphosphine (79.0 mg, 300 μmol) and carbon tetrabromide (99.0 mg, 299 μmol) were added at room temperature and stirred overnight. The reaction was quenched with the addition of pentane and filtered. The filtrate was concentrated, the resultant crude was subjected to flash chromatography with silica column and 5% ether in pentane was used as eluent. The pure fractions as identified by TLC were combined and concentrated. Due to the volatile nature of the product only mild vacuum should be employed to remove the solvents to yield 26 (71.0 mg, 93%) as colorless liquid. $R_f$=0.54 (10% ethyl ether in pentane). $^1$H NMR (400 MHz, CD$_2$Cl$_2$) δ 8.44 (d, J=2.4 Hz, 1H), 7.57 (dd, J=8.3, 2.4 Hz, 1H), 7.49 (d, J=8.3 Hz, 1H), 4.55 (s, 2H). $^{13}$C NMR (101 MHz, CD$_2$Cl$_2$) δ 159.0, 148.2 (q, J=1.6 Hz), 135.9 (q, J=1.2 Hz), 125.1, 123.7, 122.3 (q, J=274 Hz), 33.5, 27.7 (q, J=41.8 Hz). $^{19}$F NMR (376 MHz, CD$_2$Cl$_2$) δ −65.99 (s). HRMS (ESI$^+$) calcd for C$_8$H$_6$BrF$_3$N$_3$$^+$ [M+H]$^+$ 279.9692, found: 279.9688.

2-(bromomethyl)-5-(3-(trifluoromethyl)-3H-diazirin-3-yl)pyrimidine (27)

To a solution of 2 (30.0 mg, 137 μmol) in anhydrous dichloromethane (1.5 mL) at 0° C., phosphorus tribromide (44.4 mg, 164 μmol) was added slowly. The reaction was slowly warmed to RT and stirred overnight. The reaction was quenched with dropwise addition of saturated aqueous sodium bicarbonate and extracted between dichloromethane and aqueous sodium bicarbonate (the aqueous layer was extracted with dichloromethane 3 times). The combined organic layer was dried with anhydrous sodium sulfate and concentrated. Due to the volatile nature of the product only mild vacuum should be employed to remove the solvents to yield 27. The product obtained was used without further purification for the next step.

5-(2-oxohexahydro-1H-thieno[3, 4-d]imidazol-4-yl)-N-(6-((4-(3-(trifluoromethyl)-3H-diazirin-3-yl)benzyl)amino)hexyl)pentanamide (33)

To a solution of 23 (53.0 mg, 0.155 mmol) in anhydrous DMF (1.5 mL), a solution of 25 (20 mg, 71.7 μmol) in DMF (0.5 mL) was added slowly at room temperature and stirred for 3 hours. The reaction mixture was diluted with acetonitrile (10 mL) and subjected to reverse phase preparative HPLC purification. The fractions with the desired compound were collected and concentrated by removal of acetonitrile on a rotary evaporator and freeze drying the resultant aqueous solution to yield a white powder of 33 (10.1 mg, 22%) as a TFA salt. This salt was used for the next step without further purification.

(2R,3S,4S,5S,6S)-2-(acetoxymethyl)-6-(2-oxo-2-((6-(5-(2-oxohexahydro-1H-thieno[3,4-d]imidazol-4-yl)pentanamido)hexyl)(4-(3-(trifluoromethyl)-3H-diazirin-3-yl)benzyl)amino)ethoxy)tetrahydro-2H-pyran-3,4,5-triyl triacetate (36)

To a solution of TFA salt of 33 (10.0 mg, 15.7 μmol) in anhydrous DMF (1 mL), 24 (16.0 mg, 39.4 μmol), EDC (7.1 mg, 37.0 μmol) and DMAP (5.0 mg, 40.9 μmol) were added at room temperature and stirred overnight. The reaction mixture was diluted with acetonitrile (10 mL) and subjected to reverse phase preparative HPLC purification. The fractions with the desired compound were collected and concentrated by removal of acetonitrile on a rotary evaporator and freeze drying the resultant aqueous solution to yield 36 (7.5 mg, 51%) as white amorphous solid. The NMR analysis indicated the existence of 36 as rotamers. $^1$H NMR (600 MHz, CD$_3$OD) δ 7.37 (d, J=8.1 Hz, 2H), 7.26 (d, 8.1 Hz, 2H), 5.40-5.17 (m, 3H), 4.99 (d, J=1.5 Hz, 1H), 4.68-4.60 (m, 2H), 4.52-4.46 (m, 2H), 4.43-4.21 (m, 3H), 4.21-4.09 (m, 2H), 4.04-3.97 (m, 1H), 3.36-3.32 (m, 1H), 3.29-3.25 (m, 1H), 3.23-3.17 (m, 1H), 3.17-3.10 (m, 2H), 2.92 (ddd, J=12.7, 4.9, 3.7 Hz, 1H), 2.70 (d, J=12.7 Hz, 1H), 2.21-2.16 (m, 2H), 2.16-2.11 (m, 3H), 2.08-1.98 (m, 6H), 1.98-1.94 (m, 3H), 1.77-1.52 (m, 6H), 1.51-1.39 (m, 4H), 1.36-1.26 (m, 4H). $^{13}$C NMR (126 MHz, CDCl$_3$) δ 170.9, 170.8, 170.3, 170.2, 169.9, 169.8, 138.8, 137.8, 129.1, 128.5, 128.4, 127.5, 127.0, 126.8, 122.1 (q, J=275 Hz), 97.8, 69.3, 69.1, 65.9, 65.9, 65.4, 65.2, 62.4, 61.3, 61.0, 55.4, 49.9, 48.2, 46.9, 46.5, 40.4, 39.6, 39.5, 35.4, 29.8, 29.3, 29.0, 28.5, 27.7, 27.0, 26.5, 26.2, 25.4, 20.9, 20.9, 20.9, 20.8, 20.8. $^{19}$F NMR (376 MHz, CDCl$_3$) δ −65.31 (s). HRMS (ESI$^+$) calcd for C$_{41}$H$_{55}$F$_3$N$_6$NaO$_{13}$S$^+$ [M+Na]$^+$ 951.3392, found: 951.3418.

5-(2-oxohexahydro-1H-thieno[3, 4-d]imidazol-4-yl)-N-(6-(N-(4-(3-(trifluoromethyl)-3H-diazirin-3-yl)benzyl)-2-(((2S,3S,4S,5S,6R)-3, 4, 5-trihydroxy-6-(hydroxymethyl)tetrahydro-2H-pyran-2-yl)oxy)acetamido)hexyl)pentanamide (20)

To a solution of 36 (6.2 mg, 6.67 μmol) in anhydrous methanol (0.5 mL), 25% sodium methoxide in methanol solution (40 μL) was added and let to stir for 3 hours at room temperature. The reaction was quenched with the addition of 0.1% TFA in methanol solution (5 mL) and subjected to reverse phase preparative HPLC purification. The fractions with the desired compound were collected and concentrated by removal of acetonitrile on a rotary evaporator and freeze drying the resultant aqueous solution to yield 20 (2.5 mg, 49%) as white amorphous solid. The NMR analysis indicated the existence of 20 as rotamers. $^1$H NMR (600 MHz, CD$_3$OD) δ 7.34 (d, J=7.2 Hz, 2H), 7.22 (d, J=7.2 Hz, 2H), 4.85 (d, J=1.6 Hz, 1H), 4.61 (d, J=8.6 Hz, 2H), 4.49-4.38 (m, 2H), 4.32-4.25 (m, 1.5H), 3.93 (dd, J=3.4, 1.7 Hz, 0.5H), 3.86-3.81 (m, 1H), 3.76-3.70 (m, 1H), 3.69-3.41 (m, 3H), 3.26-3.21 (m, 1H), 3.20-3.15 (m, 1H), 3.14-3.09 (m, 2H), 2.93-2.88 (m, 1H), 2.67 (d, J=8.7 Hz, 1H), 2.16 (t, J=7.3 Hz, 2H), 1.74-1.37 (m, 10H), 1.32-1.24 (m, 5H). $^{13}$C NMR (126 MHz, CD$_3$OD) δ 176.0, 171.4, 166.1, 141.2, 140.5, 129.5, 128.9, 128.6, 128.2, 127.8, 101.4, 75.4, 75.2, 72.4, 72.4, 71.7, 68.6, 68.4, 66.5, 65.6, 65.2, 63.4, 63.0, 62.8, 61.6, 57.0, 41.0, 40.1, 36.8, 30.3, 29.8, 29.5, 29.4, 28.1, 27.6, 27.5, 27.4, 26.9. $^{19}$F NMR (376 MHz, CD$_3$OD) δ −65.42 (s), −65.48 (s). HRMS (ESI$^+$) calcd for C$_{33}$H$_{47}$F$_3$N$_6$NaO$_9$S$^+$ [M+Na]$^+$ 783.2970, found: 783.2973.

5-(2-oxohexahydro-1H-thieno[3, 4-d]imidazol-4-yl)-N-(6-(((5-(3-(trifluoromethyl)-3H-diazirin-3-yl)pyridin-2-yl)methyl)amino)hexyl)pentanamide (34)

To a solution of 23 (70.0 mg, 205 μmol) in anhydrous DMF (2 mL), a solution of 26 (20 mg, 71.4 μmol) in anhydrous DMF (0.5 mL) was added dropwise at room temperature and stirred for 3 hours. The reaction mixture was diluted with acetonitrile (10 mL) and subjected to reverse phase preparative HPLC purification. The fractions with the desired compound were collected and concentrated by removal of acetonitrile on a rotary evaporator and freeze drying the resultant aqueous solution to yield white powder of 34 (13.0 mg, 29%) as a TFA salt. This salt was used for the next step without further purification.

(2R,3R,4S,5S,6S)-2-(acetoxymethyl)-6-(2-oxo-2-((6-(5-(2-oxohexahydro-1H-thieno[3,4-d]imidazol-4-yl)pentanamido)hexyl)((5-(3-(trifluoromethyl)-3H-diazirin-3-yl)pyridin-2-yl)methyl)amino)ethoxy)tetrahydro-2H-pyran-3,4,5-triyl triacetate (37)

To a solution of the TFA salt of 34 (7.0 mg, 11.0 μmol) in DMF (1 mL), 24 (11.2 mg, 27.6 μmol), EDC (5.0 mg, 26.1 μmol) and DMAP (3.5 mg, 28.6 μmol) were added at room temperature and stirred overnight. The reaction mixture was extracted between brine and ethyl acetate (the aqueous layer was extracted with ethyl acetate 3 times) and the combined organic layer was dried with anhydrous sodium sulfate and concentrated. The resultant crude was subjected to reverse phase preparative HPLC purification. The fractions with the desired compound were collected and concentrated by removal of acetonitrile on a rotary evaporator and freeze drying the resultant aqueous solution to yield 37 (7.5 mg, 73%) as white amorphous solid. The NMR analysis indicated the existence of 37 as rotamers in 1:1 ratio. $^1$H NMR (600 MHz, CDCl$_3$) δ 8.45 (s, 0.5H), 8.40 (s, 0.5H), 7.61 (d, J=8.0 Hz, 0.5H), 7.57 (d, J=8.0 Hz, 0.5H), 7.37 (d, J=8.0 Hz, 0.5H), 7.27 (d, J=8.0 Hz, 0.5H), 6.77-6.67 (m, 0.5H), 6.29 (s, 0.5H), 6.13 (s, 0.5H), 5.37-5.24 (m, 2.5H), 5.19-5.13 (m, 1H), 5.01-4.88 (m, 1H), 4.73-4.55 (m, 3H), 4.43-4.31 (m, 3H), 4.29-4.20 (m, 1H), 4.15-3.96 (m, 2H), 3.41-3.11 (m, 5H), 2.99-2.87 (m, 1H), 2.77 (t, J=13.6 Hz, 1H), 2.32-2.17 (m, 2H), 2.14 (d, 3H), 2.10-2.02 (m, 6H), 1.98 (d, 3H), 1.77-1.56 (m, 5H), 1.54-1.39 (m, 5H), 1.35-1.21 (m, 4H). $^{13}$C NMR (126 MHz, CDCl$_3$) δ 174.0, 173.8, 170.9, 170.8, 170.2, 170.1, 169.8, 168.9, 168.4, 158.4, 157.8, 148.0, 146.9, 138.0, 125.1, 124.9, 124.7, 122.9, 122.7, 120.9, 120.7, 97.9, 97.8, 69.3, 69.2, 69.1, 66.0, 65.9, 65.1, 62.4, 60.9, 60.8, 55.5, 51.9, 50.3, 48.1, 46.8, 40.5, 40.4, 39.5, 39.4, 35.7, 35.5, 29.4, 29.2, 28.7, 27.9, 27.8, 27.3, 27.1, 27.0, 26.6, 26.5, 26.3, 25.5, 21.0, 20.9, 20.8, 20.7. HRMS (ESI$^+$) calcd for C$_{40}$H$_{55}$F$_3$N$_7$O$_{13}$S$^+$ [M+H]$^+$ 930.3525, found: 930.3532.

5-(2-oxohexahydro-1H-thieno[3, 4-d]imidazol-4-yl)-N-(6-(N-((5-(3-(trifluoromethyl)-3H-diazirin-3-yl)pyridin-2-yl)methyl)-2-(((2S,3S,4S,5S,6R)-3, 4, 5-trihydroxy-6-(hydroxymethyl)tetrahydro-2H-pyran-2-yl)oxy)acetamido) hexyl)pentanamide (21)

To a solution of 37 (7.5 mg, 8.06 µmol) in anhydrous methanol (0.9 mL), 25% sodium methoxide in methanol solution (10 µL) was added and let to stir for 3 hours at room temperature. The reaction was quenched with the addition of 0.1% TFA in methanol solution (3 mL) and subjected to reverse phase preparative HPLC purification. The fractions with the desired compound were collected and concentrated by removal of acetonitrile on a rotary evaporator and freeze drying the resultant aqueous solution to yield 21 (3.8 mg, 62%) as white amorphous solid. The NMR analysis indicated the existence of 21 as rotamers. $^1$H NMR (500 MHz, CD$_3$OD) δ 8.49 (s, 0.5H), 8.43 (s, 0.5H), 7.78-7.68 (m, 1H), 7.49-7.40 (m, 1H), 4.86 (s, 4H), 4.74-4.70 (m, 2H), 4.53-4.36 (m, 3H), 4.34-4.28 (m, 1H), 3.98-3.82 (m, 2H), 3.80-3.52 (m, 5H), 3.42-3.33 (m, 2H), 3.25-3.12 (m, 3H), 2.97-2.89 (m, 1H), 2.74-2.68 (m, 1H), 2.25-2.16 (m, 2H), 1.79-1.56 (m, 5H), 1.56-1.39 (m, 5H), 1.38-1.24 (m, 4H). $^{13}$C NMR (126 MHz, CD$_3$OD) (176.0, 175.9, 171.9, 171.5, 166.1, 160.7, 160.0, 148.9, 148.3, 137.0, 136.9, 125.4, 125.0, 123.3, 123.2 (q, J=274 Hz), 123.0, 101.4, 75.4, 75.2, 72.4, 71.7, 68.6, 68.5, 65.7, 65.2, 63.4, 63.0, 62.9, 61.6, 57.0, 52.5, 51.8, 47.9, 41.0, 40.1, 36.8, 30.3, 30.2, 29.8, 29.5, 28.2, 27.6, 27.5, 27.4, 26.9. $^{19}$F NMR (376 MHz, CD$_3$OD) δ −67.44 (s), −67.53 (s). HRMS (ESI$^+$) calcd for C$_{32}$H$_{46}$F$_3$N$_7$NaO$_9$S$^+$ [M+Na]$^+$ 784.2922, found: 784.2924.

5-(2-oxohexahydro-1H-thieno[3, 4-d]imidazol-4-yl)-N-(6-(((5-(3-(trifluoromethyl)-3H-diazirin-3-yl)pyrimidin-2-yl)methyl)amino)hexyl)pentanamide (35)

To a solution of 23 (70.0 mg, 205 µmol) in anhydrous DMF (1.5 mL), a solution of 27 (137 µmol) in anhydrous DMF (0.5 mL) was added dropwise slowly at room temperature and stirred for 6 hours. The reaction mixture was diluted with acetonitrile (10 mL) and subjected to reverse phase preparative HPLC purification. The fractions with the desired compound were collected and concentrated by removal of acetonitrile on a rotary evaporator and freeze drying the resultant aqueous solution to yield white powder of 35 (37.2 mg, 42%) as a TFA salt. This salt was used for the next step without further purification.

(2R,3S,4S,5S,6S)-2-(acetoxymethyl)-6-(2-oxo-2-((6-(5-(2-oxohexahydro-1H-thieno[3, 4-d]imidazol-4-yl)pentanamido)hexyl) ((5-(3-(trifluoromethyl)-3H-diazirin-3-yl)pyrimidin-2-yl)methyl)amino) ethoxy) tetrahydro-2H-pyran-3,4,5-triyl triacetate (38)

To a solution of 24 (16.0 mg, 39.4 µmol) in anhydrous DMF (2 mL), EDC (8.50 mg, 44.3 µmol) and DMAP (5.70 mg, 46.7 µmol) were added at room temperature and stirred for 10 minutes. This solution was then added to a solution of TFA salt of 35 (15 mg, 23.4 µmol) in anhydrous DMF (0.5 mL) and stirred overnight. The reaction mixture was extracted between brine and ethyl acetate (the aqueous layer was extracted with ethyl acetate 3 times) and the combined organic layer was dried with anhydrous sodium sulfate and concentrated. The resultant crude was subjected to reverse phase preparative HPLC purification. The fractions with the desired compound were collected and concentrated by removal of acetonitrile on a rotary evaporator and freeze drying the resultant aqueous solution to yield 38 (15.6 mg, 71%) as white amorphous solid. The NMR analysis indicated the existence of 38 as rotamers. $^1$H NMR (500 MHz, CD$_3$OD) δ 8.75 (s, 1H), 8.70 (s, 1H), 5.41-5.16 (m, 3H), 5.08-5.03 (m, 1H), 4.98 (d, J=1.6 Hz, 1H), 4.85-4.75 (m, 2H), 4.53-4.47 (m, 2H), 4.44 (d, J=2.3 Hz, 1H), 4.33-4.28 (m, 1H), 4.26-3.99 (m, 4H), 3.50-3.40 (m, 2H), 3.23-3.12 (m, 3H), 2.93 (ddd, J=12.7, 4.9, 3.8 Hz, 1H), 2.71 (d, J=12.7 Hz, 1H), 2.22-2.17 (m, 2H), 2.16-2.11 (m, 3H), 2.09-2.02 (m, 6H), 1.97-1.93 (m, 3H), 1.76-1.58 (m, 5H), 1.57-1.27 (m, 10H). $^{13}$C NMR (126 MHz, CD$_3$OD) δ 175.9, 175.9, 172.3, 172.3, 171.5, 171.4, 171.4, 171.3, 171.3, 171.3, 171.0, 169.0, 168.7, 166.1, 157.7, 157.3, 123.5, 123.0 (q, J=275 Hz), 122.9, 98.9, 98.9, 70.6, 70.5, 70.4, 70.3, 70.3, 70.1, 67.1, 66.9, 66.9, 66.9, 63.4, 63.3, 61.6, 57.0, 57.0, 53.6, 52.6, 41.0, 40.2, 40.2, 36.8, 30.3, 30.3, 29.8, 29.8, 29.7, 29.5, 29.5, 28.1, 27.7, 27.6, 27.5, 26.9, 20.7, 20.7, 20.6, 20.6, 20.6, 20.5. $^{19}$F NMR (376 MHz, CD$_3$OD) δ −66.08, −66.22. HRMS (ESI$^+$) calcd for C$_{39}$H$_{53}$F$_3$N$_8$NaO$_{13}$S$^+$ [M+Na]$^+$ 953.3297, found: 953.3305.

5-(2-oxohexahydro-1H-thieno[3, 4-d]imidazol-4-yl)-N-(6-(N-((5-(3-(trifluoromethyl)-3H-diazirin-3-yl)pyrimidin-2-yl)methyl)-2-(((2S,3S,4S,5S,6R)-3, 4, 5-trihydroxy-6-(hydroxymethyl)tetrahydro-2H-pyran-2-yl)oxy)acetamido)hexyl)pentanamide (22)

To a solution of 38 (6.8 mg, 7.30 µmol) in anhydrous methanol (1 mL), 25% sodium methoxide in methanol solution (10 µL) was added and let to stir for 3 hours at room temperature. The reaction was quenched with the addition of 0.1% TFA in methanol solution (3 mL) and subjected to reverse phase preparative HPLC purification. The fractions with the desired compound were collected and concentrated by removal of acetonitrile on a rotary evaporator and freeze drying the resultant aqueous solution to yield 22 (3.7 mg, 66%) as white amorphous solid. The NMR analysis indicated the existence of 22 as rotamers. $^1$H NMR (600 MHz, CD$_3$OD) δ 8.76 (s, 1H), 8.71 (s, 1H), 4.83-4.78 (m, 3H), 4.51-4.35 (m, 3H), 4.31 (dd, J=7.7, 4.5 Hz, 1H), 3.94-3.81 (m, 1.5H), 3.78-3.53 (m, 4H), 3.49-3.36 (m, 2.5H), 3.23-3.12 (m, 3H), 2.93 (ddd, J=12.7, 5.0, 3.1 Hz, 1H), 2.71 (dd, J=12.7, 3.0 Hz, 1H), 2.19 (t, J=7.4 Hz, 2H), 1.78-1.56 (m, 5H), 1.55-1.41 (m, 5H), 1.41-1.26 (m, 5H). $^{13}$C NMR (126

MHz, CD$_3$OD) δ 176.0, 175.9, 172.1, 171.7, 169.1, 168.7, 166.1, 157.6, 157.3, 123.5, 123.0 (q, J=274 Hz), 122.9, 101.3, 75.3, 75.2, 72.4, 72.3, 71.7, 71.7, 68.5, 68.5, 65.6, 65.1, 63.4, 63.0, 62.9, 61.6, 57.0, 57.0, 53.4, 52.7, 41.0, 40.2, 36.8, 30.3, 30.3, 29.8, 29.6, 29.5, 28.3, 27.7, 27.6, 27.5, 27.5, 26.9. $^{19}$F NMR (376 MHz, CD$_3$OD) δ −66.17, −66.30. HRMS (ESI$^+$) calcd for C$_{31}$H$_{46}$F$_3$N$_8$O$_9$$^+$ [M+H]$^+$ 763.3055, found: 763.3074.

General Procedure for Ambient Light Stability Evaluation.

Photolabel (1, 2, or 3) (1 mg) was dissolved in d4-methanol (500 μL) in a 5 mm NMR tube. The $^{19}$F NMR of this solution was recorded before any exposure to ambient light as the zero day reading. The NMR tube was then placed directly under two linear fluorescent lamps (28 W each) at room temperature and the $^{19}$F NMR of this solution was recorded periodically (4, 7, 14, 18, 26 and 31 days). The analysis was repeated in duplicate.

General Procedure for Thermal Stability Evaluation.

Photolabel (1, 2, or 3) (1 mg) was dissolved in d4-methanol (500 μL) in a 5 mm NMR tube. The $^{19}$F NMR of this solution was recorded before any exposure to ambient light as the zero day reading. The NMR tube was then placed in the dark at room temperature and the $^{19}$F NMR of this solution was recorded periodically (8, 14, and 31 days). The analysis was repeated in duplicate.

Procedure for Evaluation of Stability Under Incandescent Light.

Photolabel (1, 2, or 3) (1 mg) was dissolved in d4-methanol (500 μL) in a 5 mm NMR tube. The $^{19}$F NMR of this solution was recorded before any exposure to incandescent light as the zero day reading. The NMR tube was then placed directly under an incandescent lamp (65 W) at room temperature and the $^{19}$F NMR of this solution was recorded periodically (1, 3, 5 and 15 days).

General Procedure for Aqueous Solubility Measurement.

Aqueous solubility was measured using a HPLC-MS method.[27] A calibration curve was generated by plotting the area count (HPLC) against the known concentration of compound prepared by serial dilution (1000 μM to 0.017 μM) using DMSO as the solvent. For generating calibration curve in the low concentration range (0.017-1.00 μM) the area count obtained by LC-MS (selective ion mode) was used. For generating calibration curve in the high concentration range (5.00-1000 μM) the area count obtained by HPLC-DAD (UV absorbance) was used. A 100 mM solution of the compound (6 μL) was added to the 100 mM phosphate buffer solution (594 μL) (pH 7.4 or 5.0) to get a 100 fold dilution. This mixture was incubated at 21° C. for 18 hours, filtered using a membrane filter (PVDF, 0.2 μm), and injected into the HPLC. The concentration in the aqueous solution was then determined by interpolating the sample's area count with the respective calibration curve. The analysis was performed in four replicates.

General Procedure for Photolabeling.

To a solution of concanavalin A (Con A) (0.2 mg) in acetate buffer (10 mM, pH=5 with calcium chloride (1 mM), manganese (II) chloride (1 mM) and sodium chloride (200 mM)) (1 ml), the photoaffinity label (20, 21 or 22) solution (10 mM) in methanol (3 μL) was added at 0° C. This solution was bubbled with a gentle stream of nitrogen gas, using a clean needle, for 5 minutes and incubated in the dark at 0° C. for 30 minutes. The sample was then transferred to a disposable cuvette and photoactivated for 10 minutes using a 150 W XBO xenon short-arc UV lamp fitted with a filter that cuts off light with wavelengths less than 320 nm. The resultant sample can be stored at −80° C. and used for SDS gel, Western blot analysis or mass spectroscopic analysis.

Photolabeling in the Presence of Mannose.

For the competitive binding studies with mannose, to a solution of Con A (0.2 mg) in acetate buffer (10 mM, pH=5 with calcium chloride (1 mM), manganese (II) chloride (1 mM) and sodium chloride (200 mM)) (1 ml) a aqueous solution of mannose (30 μL of 100 mM solution for 100 fold [or] 30 μL of 1 M solution for 1000 fold) was added and mixed. To this the photoaffinity label (20, 21 or 22) solution (10 mM) in methanol (3 μL) was added at 0° C. This solution was bubbled with a gentle stream of nitrogen gas, using a clean needle, for 5 minutes and incubated in the dark at 0° C. for 30 minutes. The sample was then transferred to a disposable cuvette and photoactivated for 10 minutes using a 150 W XBO xenon short-arc UV lamp fitted with a filter that cuts off light with wavelengths less than 320 nm. The resultant sample can be stored at −80° C. and used for SDS gel and Western blot analysis.

General Procedure for Western Blot Analysis.

Upon running the SDS gel, the PVDF membrane and gel was shaken in transfer buffer for 15 minutes. The holder cassette was placed opened in a shallow vessel such that the black panel was lying flat on the bottom of the vessel. Fiber pad presoaked with transfer buffer was then placed on the black panel of the holder cassette and a presoaked filter paper was placed over it. The equilibrated gel was carefully placed over the filter paper to avoid any air bubble getting trapped between the layers. Then the PVDF membrane was laid over the gel with care towards avoiding any air pocket between the layers. A presoaked filter paper was placed over the membrane followed by a filter pad. The resultant sandwich was firmly secured and the cassette was closed. The cassette holder was placed in the tank such that the black panel of the holder was on the black panel electrode. Insert the ice pack on the other side of the tank and place the tank on a magnetic stirrer. The tank was filled to the top row of circles in the cassette with transfer buffer. The magnetic stirrer was turned on and the lid was closed with black wire to black panel, red wire to red panel. The unit was connected to a power supply and ran at constant voltage of 70 V for 60 minutes. The membrane was carefully removed and the membrane was blocked with 5% (w/v) NFDM (non-fat dry milk) in tris saline Tween-20 buffer (TBS-T) for 1 hour at room temperature. The blocked membrane was then incubated overnight on a shaker at 4° C. with anti-biotin-peroxidase antibody in TBS-T buffer containing 1% NFDM. The membrane was washed five times (10 minutes each time on a shaker) with TBS-T buffer. The membrane was incubated for 5 minutes at room temperature with SuperSignal West Pico chemiluminescence substrate as per manufacturer's protocol. The resultant chemiluminescence of the bands was recorded on a photographic film and developed using a film processor.

Synthesis of Photoaffinity Probes 14-19 and 20-22.

Synthesis of Photoaffinity Probes 14-19 for Solubility Studies.

Figure 11:
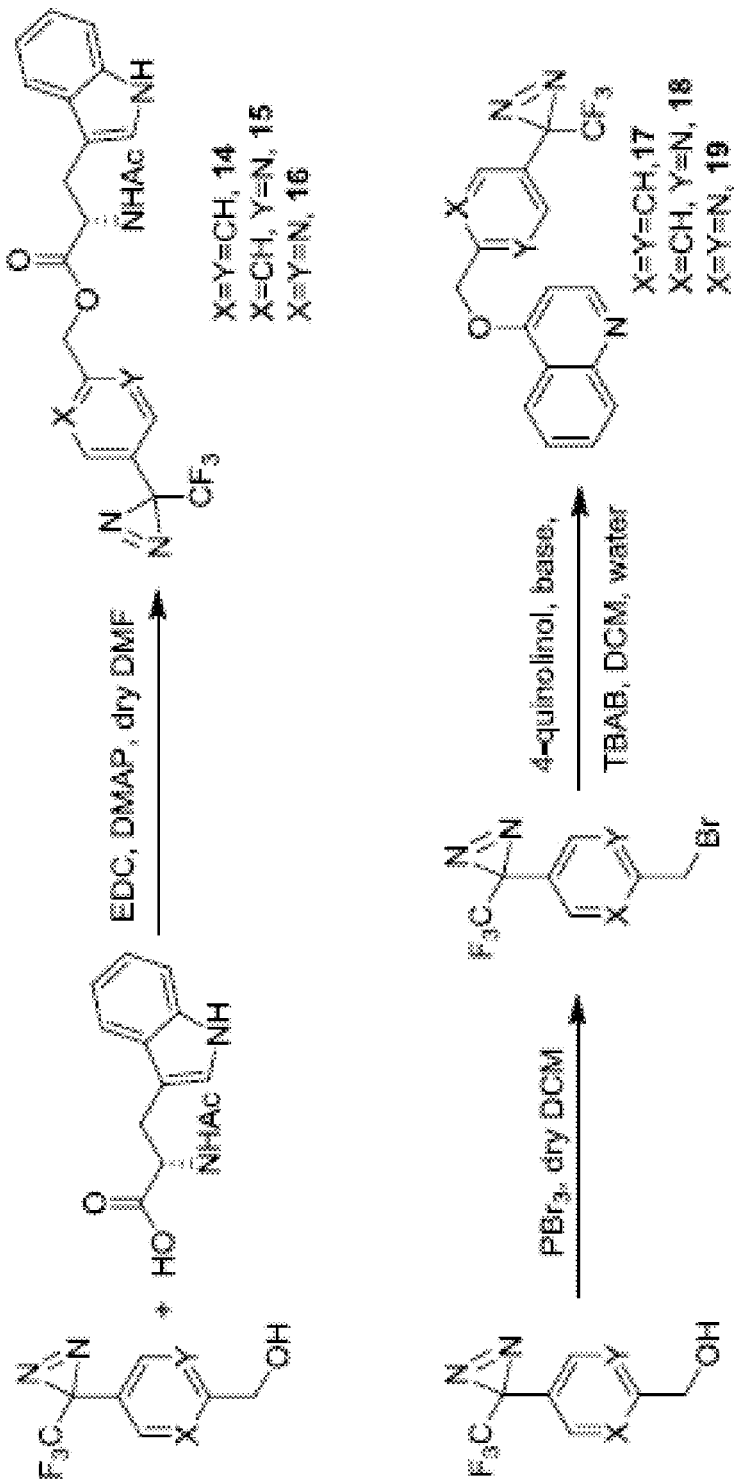
FIG. 11 shows a synthesis scheme for synthesis of photoaffinity probes 14 to 19 for solubility studies of Example 1.

Photoaffinity probes 14-19 were synthesized to evaluate the aqueous solubility (FIG. 11). The N-acetyl tryptophan derived photoaffinity probes 14, 15, and 16 were synthesized by a conventional esterification reaction using 1-ethyl-3-(3-dimethylaminopropyl)carbodiimide (EDC) coupling (FIG. 11). The quinolone derivatives 17, 18, and 19 were prepared by a two-step process in which the alcohol function of the photolabel bearing moiety was converted to the bromide using phosphorus tribromide (FIG. 11). In the second step the resultant bromide was subjected to a nucleophilic substitution reaction with quinolinol under basic conditions. The use of sodium hydroxide as base was successful in the preparation of 17 and 18, but resulted in undesired side products with pyrimidinyl derivative. Thus potassium carbonate was used to deprotonate the quinolinol for the substitution reaction with pyrimidinyl derived photo probe to obtain 19.

Synthesis of Photoaffinity Labels Based on Conventional Photolabel 3 and Modified Trifluoromethylaryl Diazirine Photolabels 1 and 2.

Figure 12:
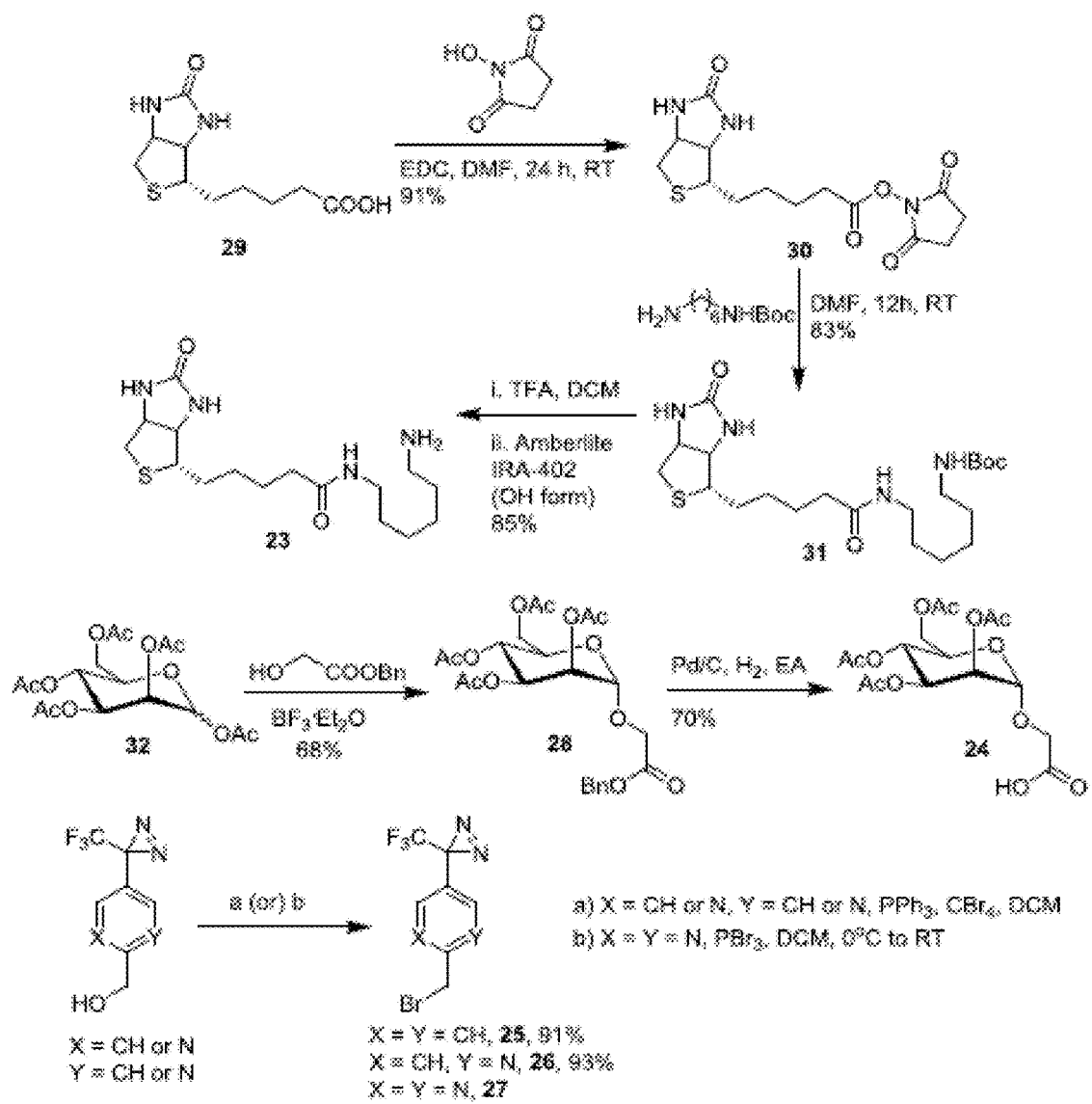
FIG. 12 shows a synthesis scheme for synthesis of intermediates 23, 24, 25, 26 and 27.

The synthesis of photoaffinity labels 20, 21, and 22 was achieved by a convergent route, in which biotin amine 23, carboxylic acid derived mannose 24, and diazirines 25, 26 and 27 were first synthesized separately as key intermediates (FIG. 12) and coupled together in the last steps of the synthesis. Biotin amine 23 was synthesized as reported earlier[1] and the free base was generated using the basic resin Amberlite IRA-402 (OH form). Benzyl ester 28 was synthesized by a boron trifluoride coupling of D-mannose pentaacetate with the corresponding alcohol in moderate yield. Benzyl ester 28 was exclusively α-mannoside as confirmed by the $^1$H NMR coupling constants. The free carboxylic acid 24 was synthesized by benzyl deprotection of 28 using Pd/C and hydrogen in good yield. The bromides 25 and 26 were synthesized from the corresponding phenyl diazirine 3 and pyridinyl diazirine 1 via the Apple reaction. In contrast, the Apple reaction did not yield bromide 27 with pyrimidinyl diazirine 2. However, the reaction of pyrimidinyl diazirine 2 with phosphorus tribromide yielded the desired bromide 27.

Figure 13:
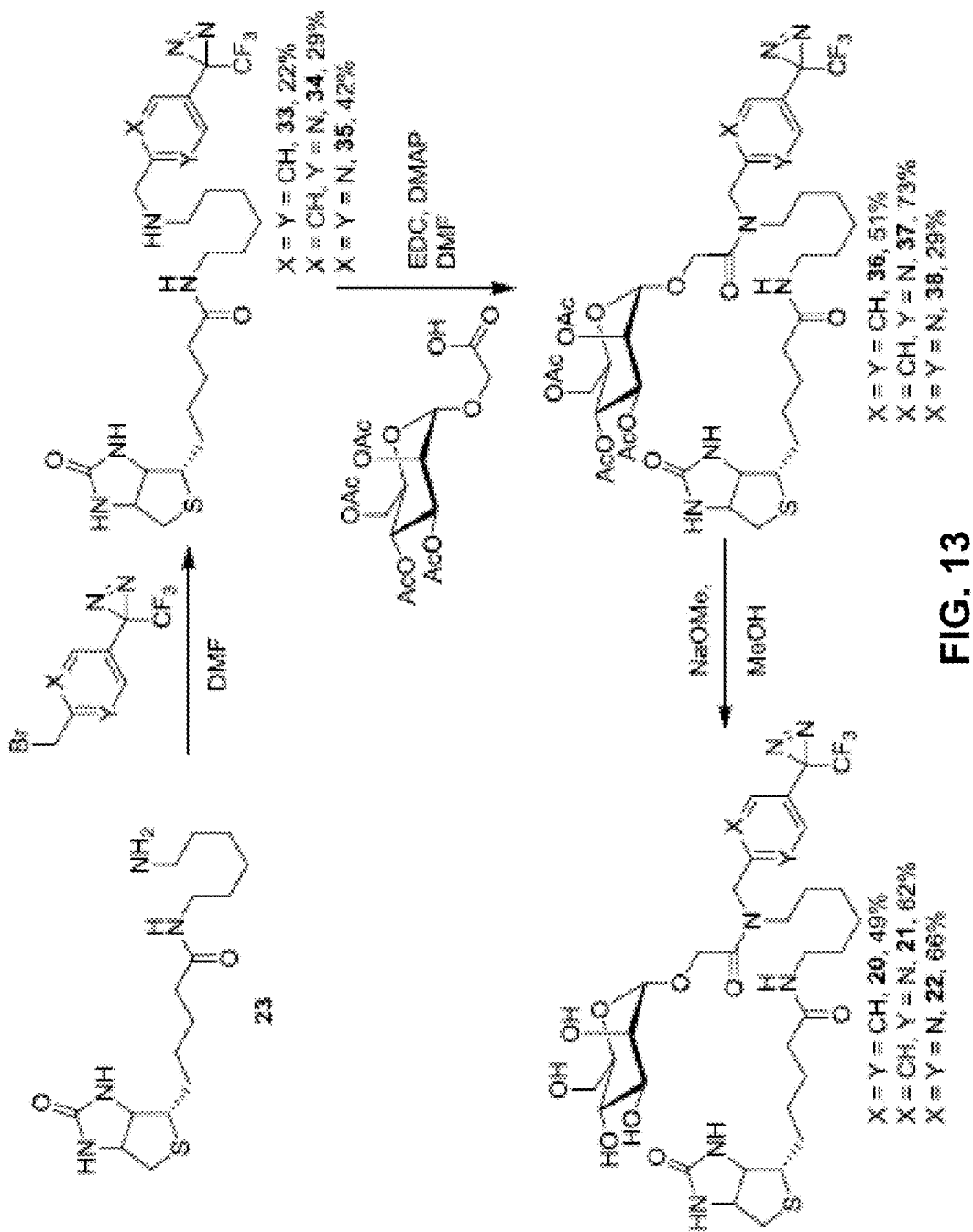
FIG. 13 shows a synthesis scheme for synthesis of synthesis of photoaffinity labels 20, 21, and 22.

In the convergent step of the synthesis, bromide 25, 26, or 27 was treated with an excess of primary amine 23 to obtain the desired secondary amine 33, 34, or 35 (FIG. 13). The corresponding secondary amine was subsequently subjected to an EDC coupling with carboxylic acid 24 to get the amide 36, 37, or 38, which was deacetylated using a catalytic amount of sodium methoxide in methanol to furnish the photoaffinity label 20, 21, or 22.

Experimental Procedures for Mass Spectrometry.

Sample Preparation.

The sample was subjected to protein precipitation by adding cold (−20° C.) acetone (1.2 mL) to the solution of photolabeled sample (0.3 mL) and vortexed. The resultant sample was incubated for 60 minutes at −20° C. The sample was placed in a centrifuge precooled in a cold room (4° C.) and centrifuged at 13,000×g for 10 minutes. The supernatant was carefully decanted without dislodging the protein pellet. The remaining acetone was allowed to evaporate by keeping the tube uncapped at room temperature for 30 minutes (the protein might not dissolve properly if the pellet was over dried). The pellet was redissolved in 50 mM ammonium bicarbonate buffer (50 μL) and 3 μg of sequencing grade modified trypsin (Promega catalog #V5111) in trypsin resuspension buffer (provided with the commercial trypsin) (10 μL) was added to it. The resultant solution was incubated at 37° C. for 18 hours followed by the addition of 5% formic acid in acetonitrile (200 μL). The solution was speed vacuumed to dryness and another portion of 5% formic acid in acetonitrile (200 μL) was added and speed vacuumed till all the liquid was removed. The resultant residue was redissolved in 0.1% formic acid aqueous solution (50 μL) and sonicated for 5 minutes. The sample was subjected to centrifugation at 5,000×g for 5 minutes and the supernatant was taken for mass spectroscopic analysis.

Mass Spectroscopic Analysis.

Peptides resulting from the digestion were analyzed by liquid chromatography mass spectrometry (LC MS). Briefly, chromatography was performed using a Nano-LC Ultra 2D+(Eksigent, Dublin, Calif.) equipped with a Proteopep 2 IntegraFrit trapping column (100 μm i.d.×2.5 cm; C18, 5 μm, 300 Å) and a Proteopep 2 IntegraFrit analytical column (75 μm i.d.×10 cm; C18, 5 μm, 300 Å, New Objective, Woburn, Mass.). Sample (5 μL for a total of 1.5 μg) was loaded onto the trap column at 3 μL/min (Solvent A) for 7 minutes, after which a valve was switched to include the analytical column. Peptides were then eluted with a gradient (300 nL/min) of 2% B to 40% B over 80 minutes (Solvent A: 0.5% formic acid in water, Solvent B: 0.5% formic acid in acetonitrile). Nano-LC effluent was analyzed on-line by positive-ion micro-electrospray with a linear ion trap Orbitrap XL (LTQ OrbiTrap XL, Thermo Fisher Corp., Bremen, Germany) operated in 'top-5 data-dependent' acquisition mode. Labeled peptides were found by subtractive analysis between non-labeled and labeled samples. MS/MS results were sequenced heuristically.

Results

Figure 2B:
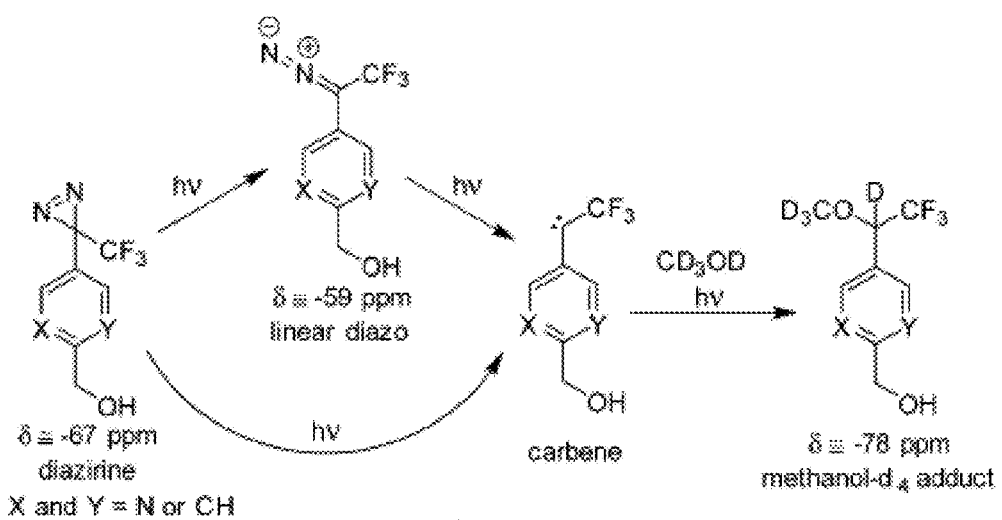

The photoactivation and the photostability of diazirines 1-3 were investigated first by $^{19}$F NMR utilizing deuterated methanol to scavenge the carbene intermediates.[19, 20] Previous $^{19}$F NMR studies have demonstrated that photoactivation of diazirine 3 lead predominantly to the corresponding singlet carbene, which rapidly forms the methanol insertion product (FIG. 2B).[14, 19] In parallel, a side reaction occurs by rearranging diazirine 3 into a linear diazo compound, which under continuous light exposure slowly decomposes to the reactive carbene leading ultimately to the methanol insertion product.

Figure 6A:
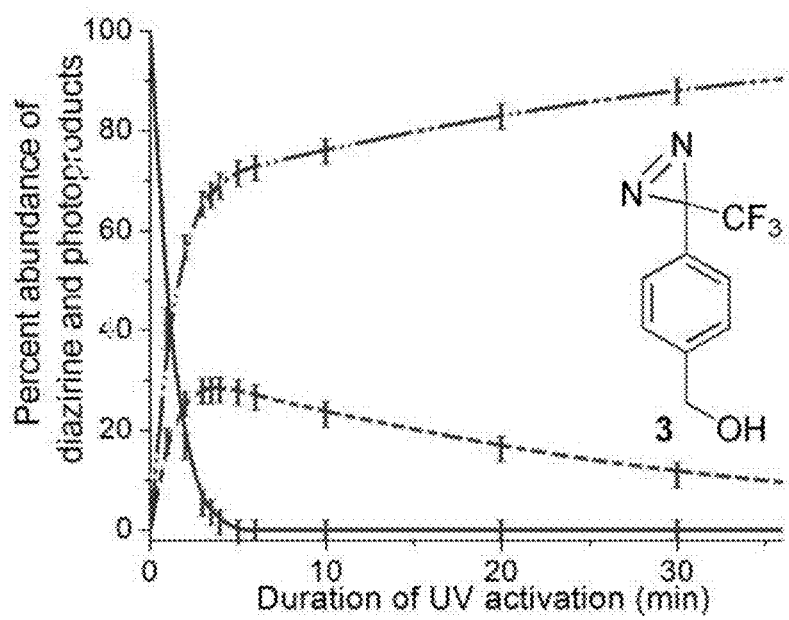
FIGS. 6A-6C shows graphs demonstrating the distribution of diazirine, linear diazo and carbene insertion product at different time intervals of UV activation. The distribution of the three species were determined by photoactivating a solution of the photolabel in $d_4$-methanol with UV light and measuring the compound distribution using $^{19}F$ NMR at different time intervals.
Figure 6B:
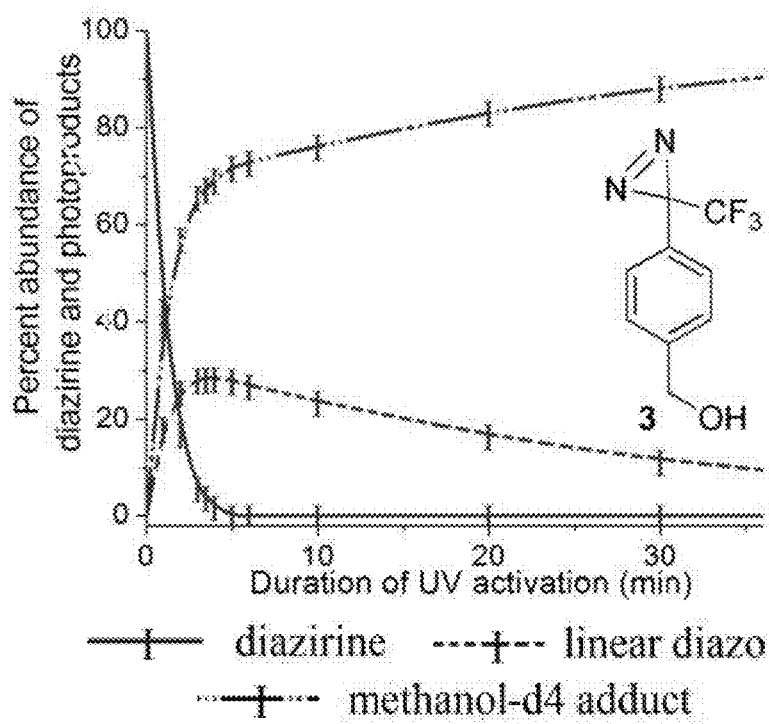
Figure 6C:
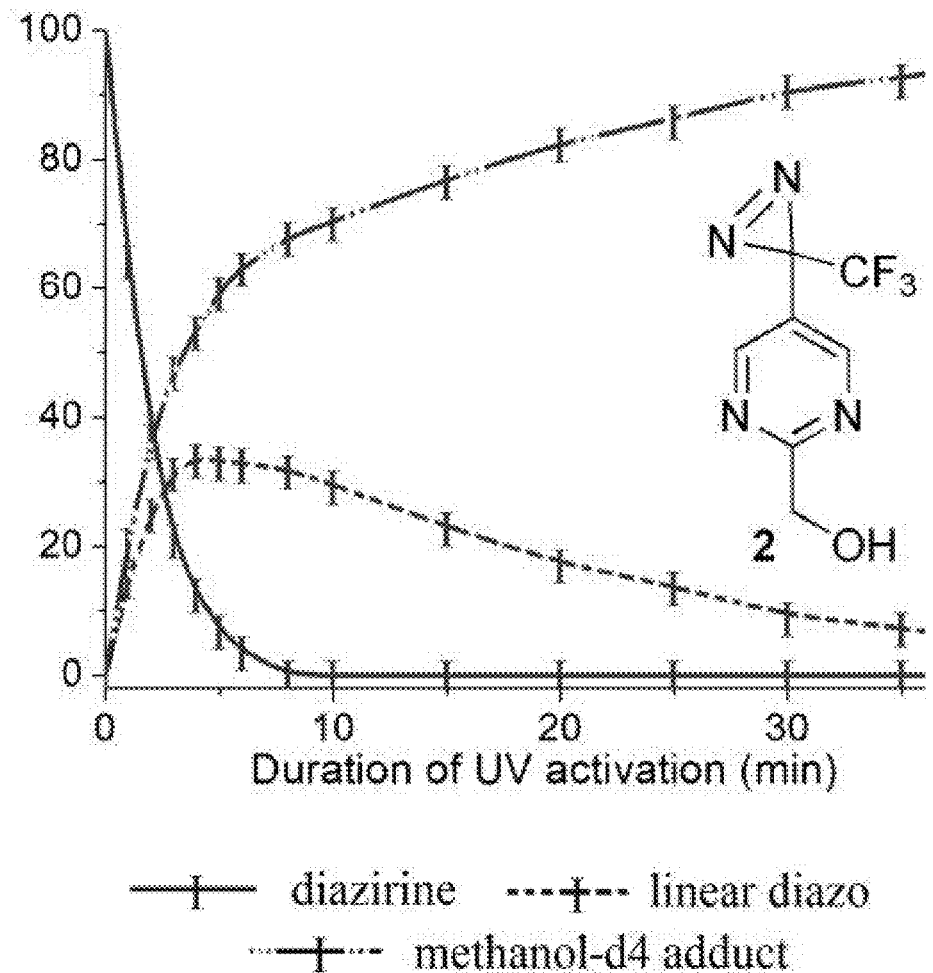

Similarly, a $^{19}$F NMR experimental set-up was chosen to monitor the photoactivation of diazirines 1-3. The exchange of the phenyl ring in the 3-trifluoromethyl-3-phenyl diazirine 3 by the electron withdrawing pyridine or pyrimidine ring did not affect the ratio between the carbene and the linear diazo intermediate (FIGS. 6A-6C). Across control compound 3 and the modified photolabels 1 and 2, the linear diazo intermediate peaked at about 30% and decreased as irradiation continued. These results indicated that the photolabeling efficiency, with respect to the ratio of carbene to linear diazo ratio, would not be affected by switching the phenyl moiety with a pyridine or a pyrimidine.

Figure 3:
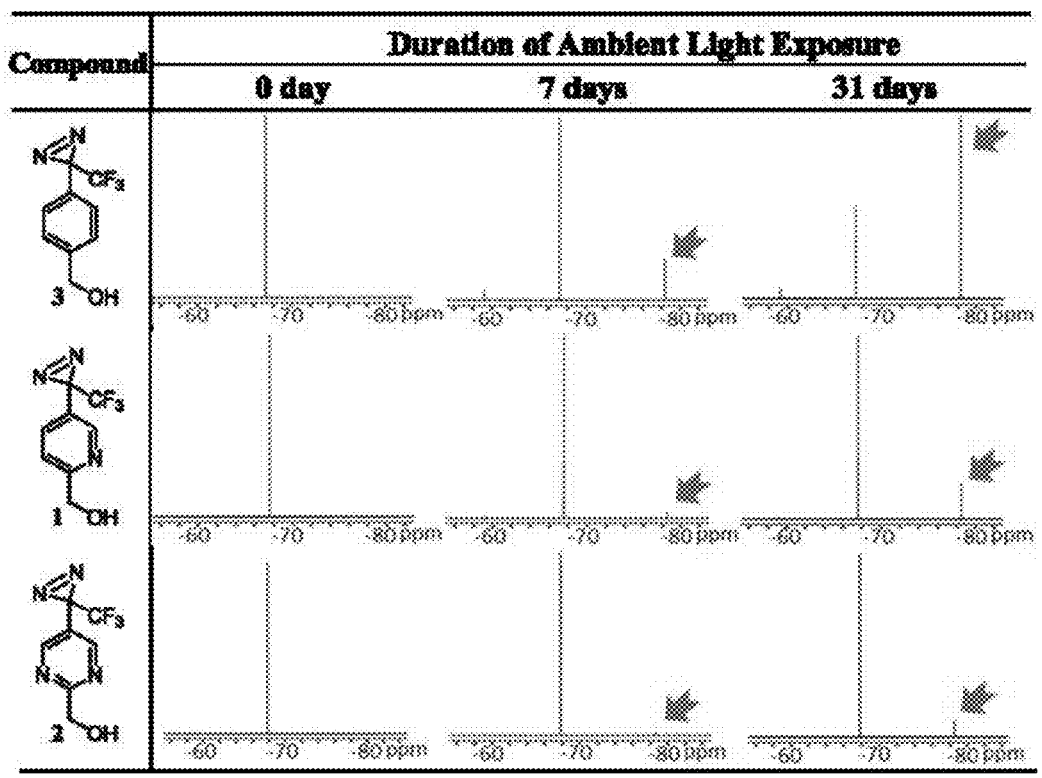
FIG. 3 shows a table demonstrating a comparison of ambient light stability of modified trifluoromethylaryl diazirines 1 and 2 versus the conventional trifluoromethylphenyl diazirine 3. A solution of trifluoromethylaryl diazirines 1, 2 or 3 in d4-methanol was exposed to light from two linear fluorescent lamps (28 W each) at room temperature and the photodecomposition of the diazirines were followed by $^{19}F$ NMR. The picture shots of the $^{19}F$ NMR shows that upon exposure to ambient light the conventional trifluoromethylphenyl diazirine decomposes faster as indicated by the decomposition product peak (pointed out by arrow), while the pyridinyl derivative is much more resistant to the photodecomposition and the pyrimidinyl diazirine is virtually intact.
Figure 9:
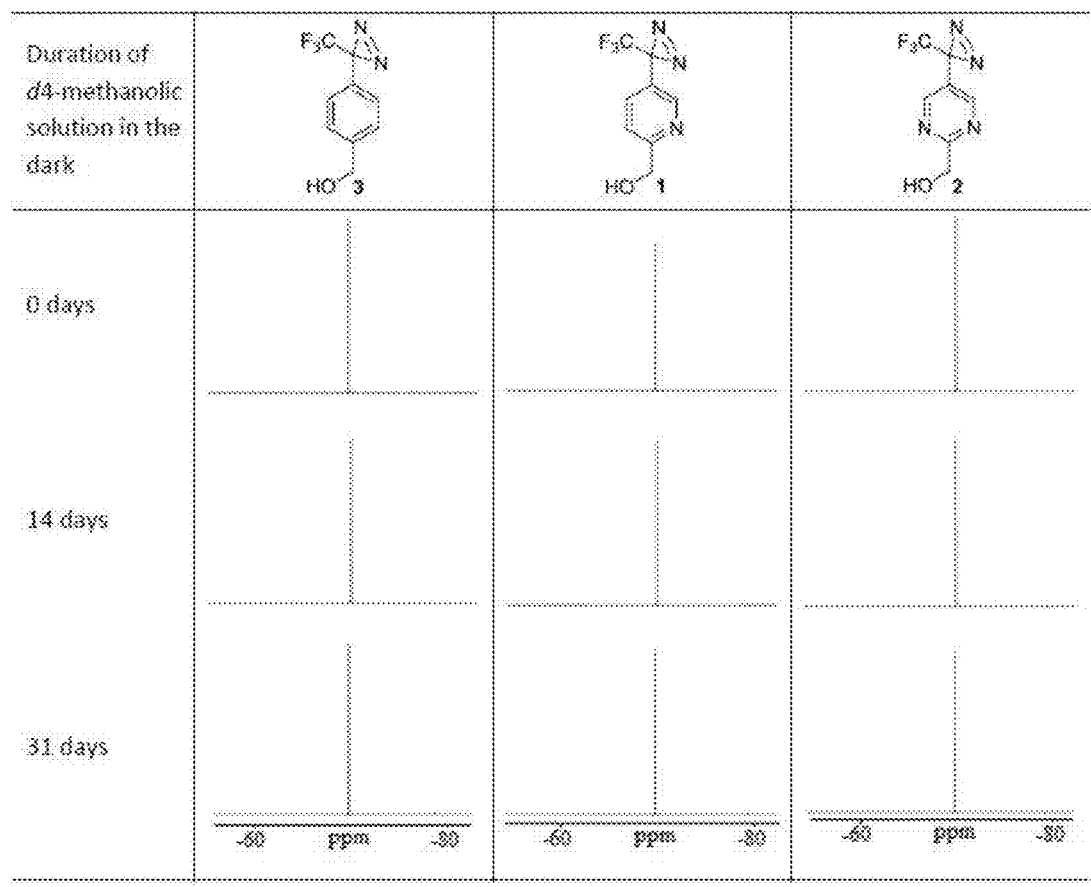
FIG. 9 shows a table demonstrating a comparison of thermal stability of d4-methanolic solution of 1, 2 and 3 in the dark at room temperature using $^{19}F$ NMR. The Table S3 shows that the conventional photolabel 3 and modified trifluoromethylaryl diazirine photolabels 1 and 2 are all stable as methanolic solutions at 21° C. in the dark.

The modified 3-trifluoromethyl-3-aryldiazirine photolabels 1 and 2 were subjected to an ambient light stability test along with the conventional 3-trifluoromethyl-3-phenyl diazirine photolabel 3 to determine the effectiveness to increase the light stability of diazirine photolabels 1 and 2. Solutions of the conventional diazirine 3 and modified photolabels 1 and 2 in deuterated methanol were exposed to ambient light conditions using linear fluorescent lamps, and the rate of decomposition was observed over a period of one month. As shown by the $^{19}$F NMR, 3-phenyl diazirine 3 had already undergone significant photodecomposition after 7 days of light exposure (FIG. 3). In contrast, during the same period of ambient light exposure, pyridine photolabel 1 negligibly photodecomposed whereas pyrimidyl photolabel 2 was virtually unaffected. Exposing the probes 1-3 to light for a period of one month continued this stability trend. As determined by $^{19}$F NMR, only 27% of the conventional photolabel 3 remained intact after one month of ambient light exposure (FIG. 7), whereas 79% of the pyridine photolabel 1 and 90% of the pyrimidine photolabel 2 remained unaffected. Similar stability trends were observed when photolabels 1-3 were exposed to light from an incandescent bulb (FIG. 8). No appreciable decomposition of diazirines 1-3 was detected in a control experiment when compounds 1-3 were kept in the dark at room temperature for a period of one month (FIG. 9), suggesting probes 1 and 2 to be equally stable compared to the conventional phenyldiazirine 3. Furthermore, the near-UV/Vis absorption spectra show that the maximum absorption $\lambda_{max}$ was 350 nm for 1-3, whereas the absorption coefficient ε was decreased by approximately 15% for pyiridine 1 and 30% for pyrimidine 2 (FIG. 10). Importantly, these results proved our hypothesis of increasing the ambient light stability by stabilizing the diazirine ring with electron withdrawing substitutions to be correct.

Figure 4A:
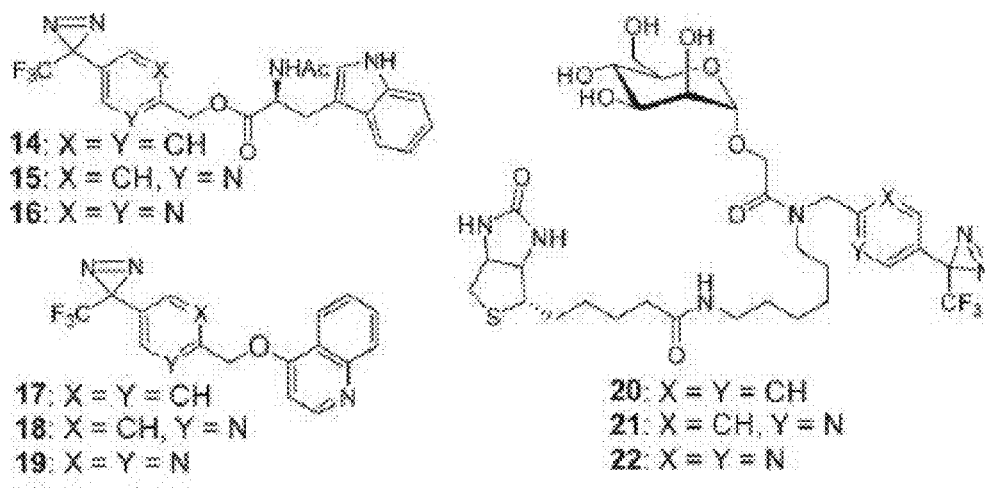
FIGS. 4A-4D show (FIG. 4A) compounds 14-19 synthesized for solubility studies and photoaffinity probes 20, 21 and 22 designed to evaluate photolabeling activities, (FIG. 4B) Coomassie stained gel of photolabeled Con A and control samples, (FIG. 4C) results of a western blot analysis to detect biotinylation of Con A through photolabeling, which indicates that Con A is photolabeled with the pyridinyl and pyrimidinyl photolabels 21 and 22 as effectively as the conventional phenyl derived photolabel 20, and (FIG. 4D) photolabeling of Con A with 21 and 22 in the presence of the native ligand mannose at different concentrations. The western blot analysis suggests that the extent of photolabeling of Con A with photoprobes 21 or 22 correlates indirectly to the concentration of competing mannose ligand.

Photolabeling experiments are commonly conducted in aqueous buffer solutions, and it was predicted that pyridine and pyrimidine probes 1 and 2 will possess a better aqueous solubility than the conventional 3-trifluoromethyl-3-phenyl diazirine 3. To demonstrate the aqueous solubility enhancements of pyridine and pyrimidine photoprobes, compounds 1-3 were derivatized with N-acetyl tryptophan or 4-quinolinol to yield corresponding esters 14-16 or ethers 17-19 (FIG. 4A). The aqueous solubility of compounds 14-19 were experimentally determined at pH=7.4 and 5.0 using a previously reported HPLC-based assay (FIG. 10).[21] As expected, in comparison to conventional 3-trifluoromethyl-3-phenyl-diazirines 14 and 17, the pyridyl probes 15 and 18 were approximately 30-250-fold more soluble, whereas pyrimidinyl probes 16 and 19 were 100-7,500 times more soluble.

When the photoaffinity probes are subjected to mass spectroscopic analysis under the conditions the peptide samples are analyzed, the major fragmentation was the loss of mannose residue in the mass spectrometer. In the same retention time that the above labeled peptide was found another peptide fragment was found (FIG. 15) with the mass corresponding to same peptide sequence (Val91-Lys101) plus the photoaffinity probe with the loss of mannose residue (FIG. 10).

To investigate whether pyridyl- and pyrimidyl-substituted diazirines 1 and 2 are suitable for photoaffinity labeling of protein targets, mannose photoaffinity probes 20-22 were designed to label concanavalin A (Con A) (FIG. 4A). Previously, a specifically designed diazirine-derived mannose photoaffinity probe was reported to covalently crosslink to Con A at the saccharide binding sites.[22] Diazirine probes 20-22 were designed with a biotin moiety to facilitate western blot visualization and post-labeling enrichment (synthesis of 20, 21 and 22 detailed in Supporting Information Scheme S3).

Figure 4B:
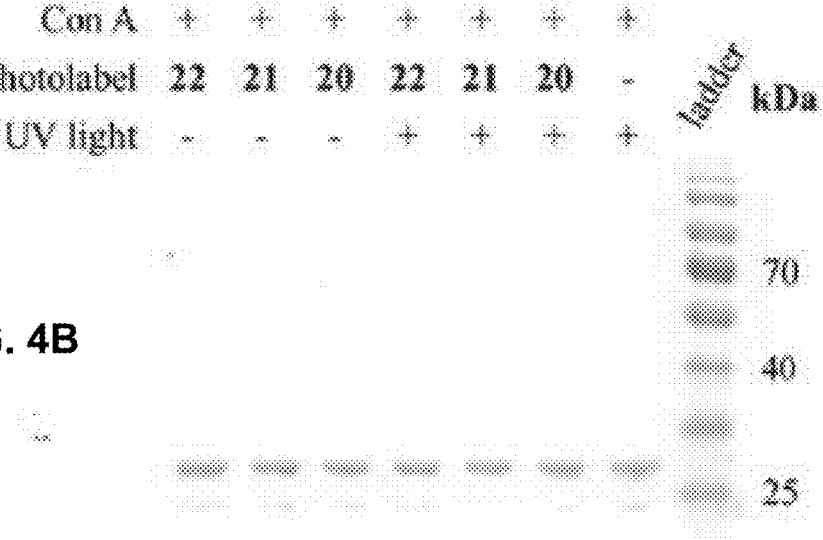
Figure 4C:
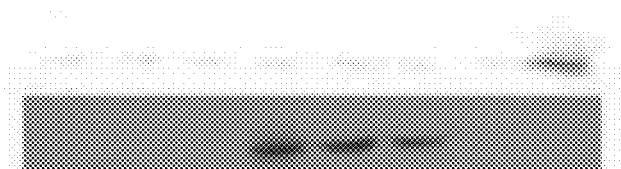

In the first labeling experiment, probes 20-22 were incubated with Con A and subjected to photoaffinity labeling by exposure to UV light (>320 nm). In another set of experiment, probes 20-22 were incubated with Con A without being exposed to UV light to investigate if there is any labelling in the absence of photoactivation. As a control, Con A in incubation buffer in absence of any photoaffinity probe was also subjected to photoactivation under UV light. The control, which contained Con A without any photoaffinity probe, was visualized with coomassie stain but did not make any visible spot in the anti-biotin peroxidase antibody western blot (FIGS. 4B and 4C). In contrast, the samples containing Con A and label 20, 21 or 22 that were photoactivated with UV light were visible with both coomassie stain and anti-biotin peroxidase antibody western blot. This data indicates that the biotin containing photoaffinity labels derived from the modified photoaffinity labels 21 and 22 and the conventional 3-trifluoromethyl-3-phenyldiazirine photoaffinity label 20 successfully labeled the protein target upon photoactivation. However, samples containing Con A along with photoaffinity labels 20, 21 or 22 that were not photoactivated with UV light were detected only with coomassie stain and not in the western blot analysis, proving that Con A is tagged only upon photoactivation of the photoaffinity probes. These data suggest that the modified labels 1 and 2 are capable of tagging proteins upon photoactivation as efficiently as the conventional diazirine photolabel 3.

Figure 4D:
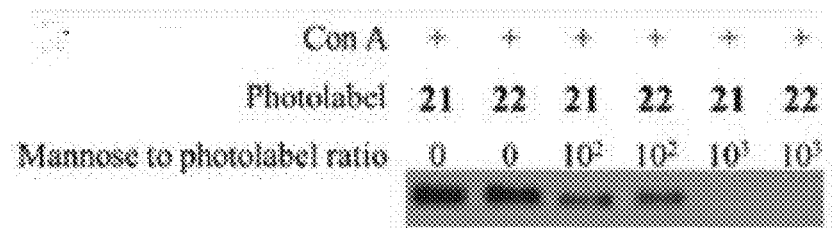

Since mannose is the natural ligand of Con A, addition of mannose prior to the photolabeling should inhibit the binding of the photoaffinity labels 20-22 to Con A and impede thephotoaffinity labeling. In presence of mannose ligand, it was observed that the crosslinking of 20-22 was significantly suppressed (FIG. 4D) depending on the concentration of mannose ligand. These results suggested that the photolabeling of 20-22 occurred at the mannose-specific binding sites of the target protein Con A and not in an unspecific way on the protein surface.

Figure 5A:
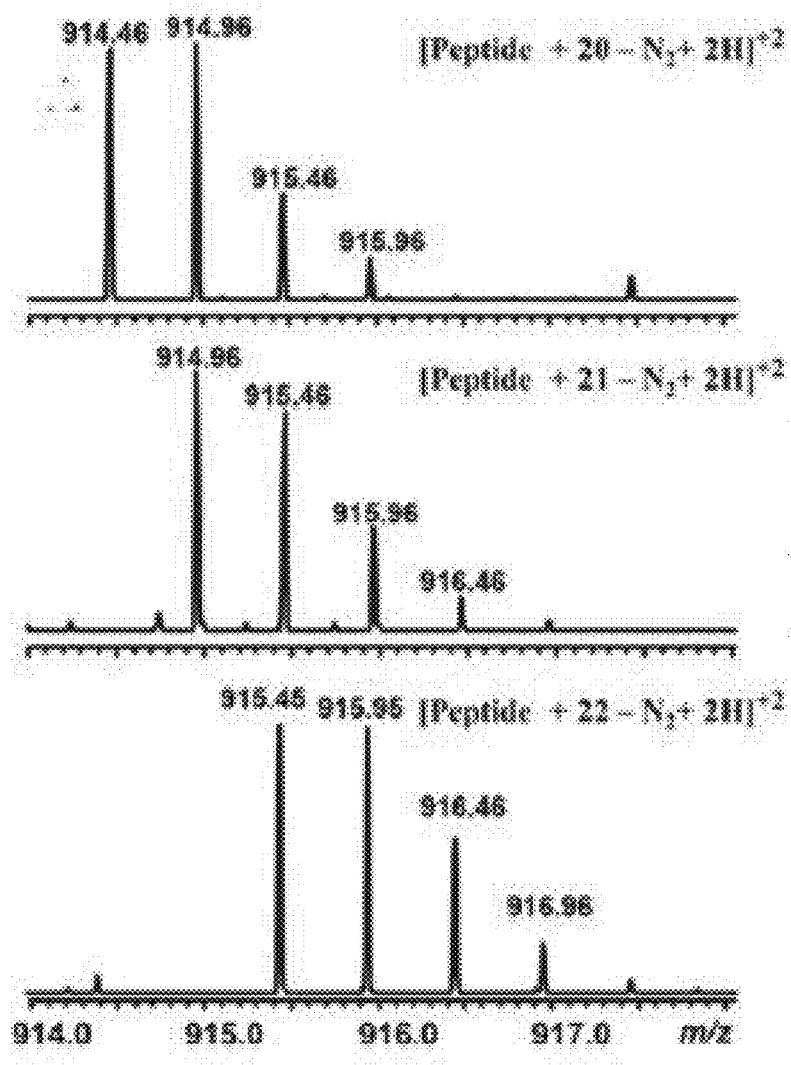
FIGS. 5A-5B show (FIG. 5A) a mass spectra of peptides labeled with photolabels 20-22. The MS/MS analysis and high accuracy mass (<3 ppm) analysis revealed that the crosslinked peptide is Val91-Lys101 (VGLSASTGLYK) residue.
Figure 5B:
Figures 14, 15:
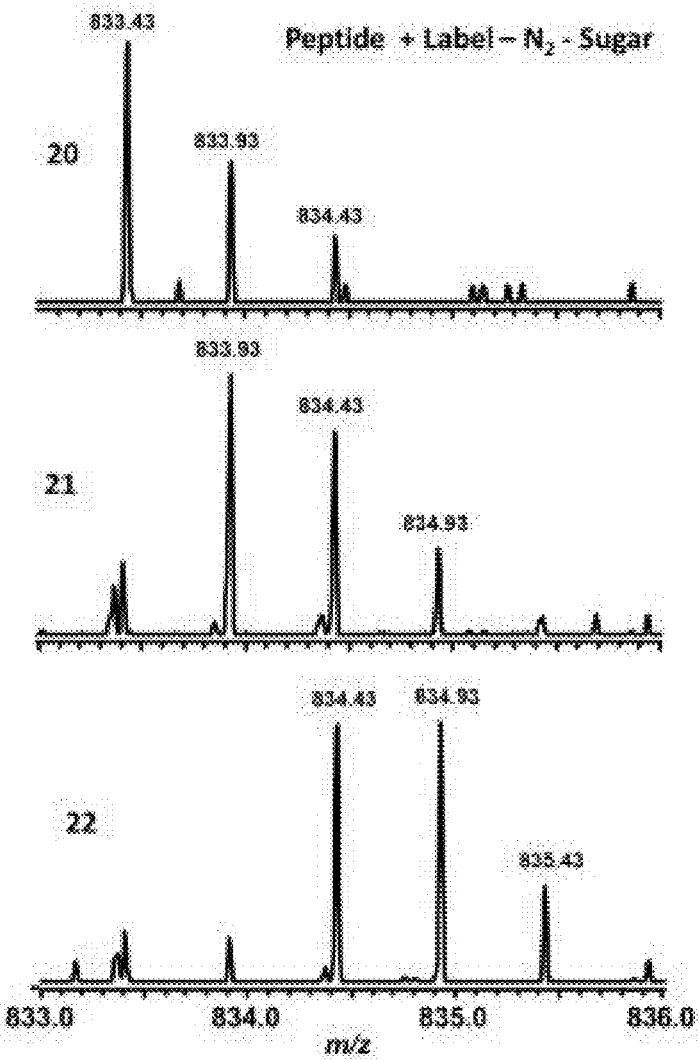
FIG. 14 shows a table demonstrating the identification of peptide sequence photolabeled with photoaffinity labels 20, 21 and 22 using high resolution mass spectrometry.
FIG. 15 shows representative spectra demonstrating a loss of mannose residue in the mass spectrometer by the peptides labeled with photolabels 20, 21 and 22.
Figures 16, 17:
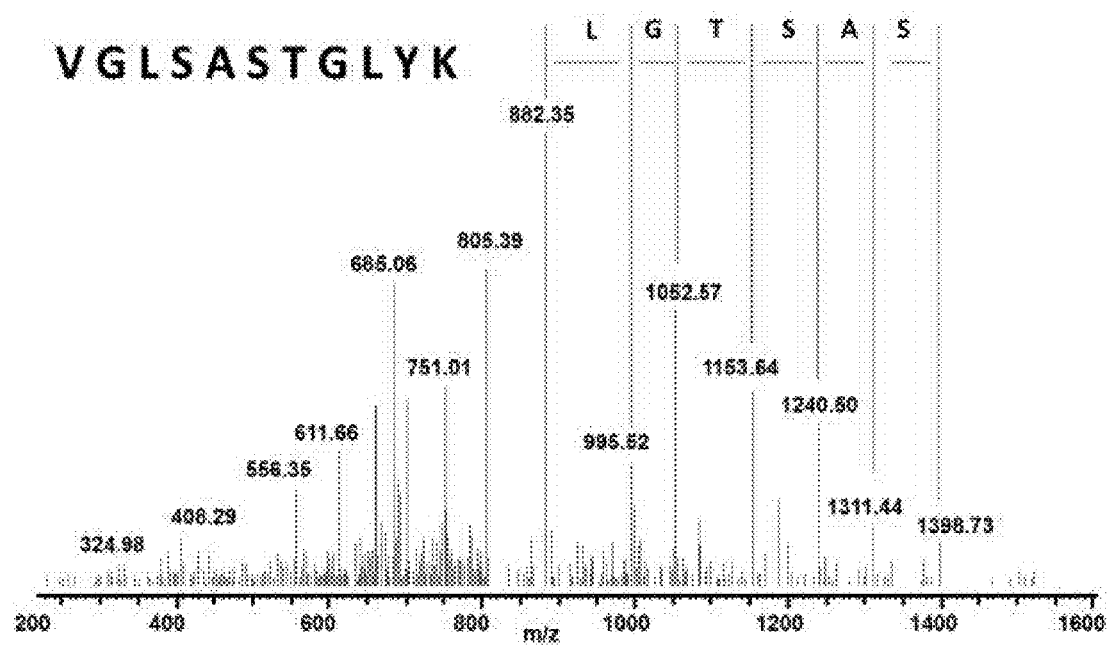
FIG. 16 shows a table demonstrating peptide fragments photolabeled with photoaffinity labels 20, 21, and 22 upon the loss of mannose residue in the mass spectrometer.
FIG. 17 shows a representative spectra demonstrating confirmation of peptide identity as confirmed by MS/MS fragmentation.
Figure 18A:
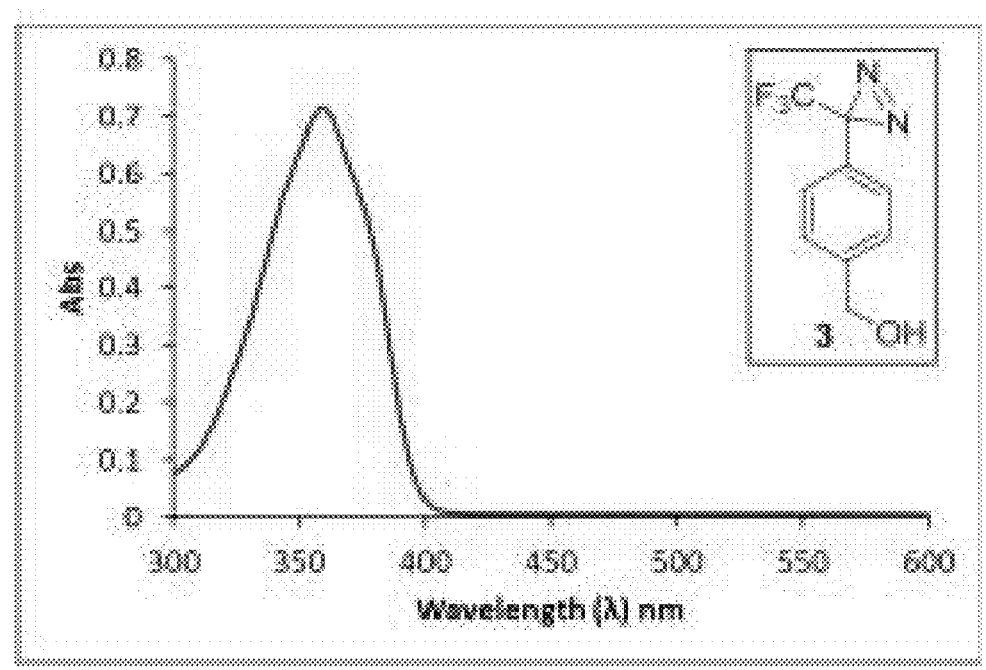
FIGS. 18A-18C show graphs demonstrating the near UV-visible spectra of photolabels 1, 2 and 3, recorded using 2.5 mM solution in methanol.
Figure 18B:
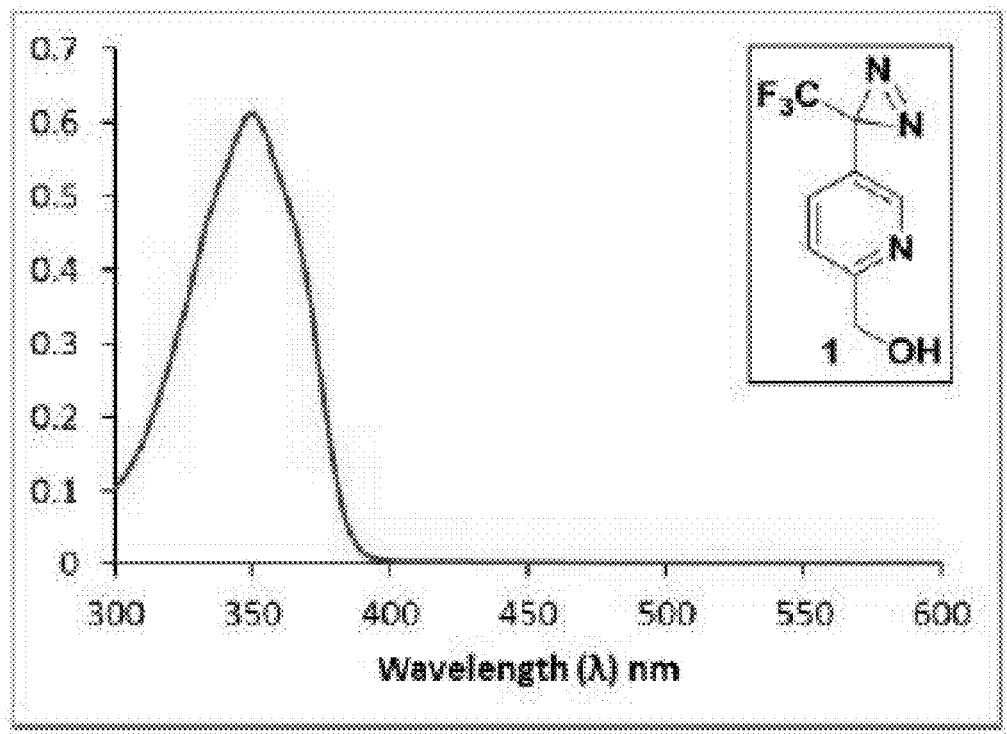
Figure 18C:
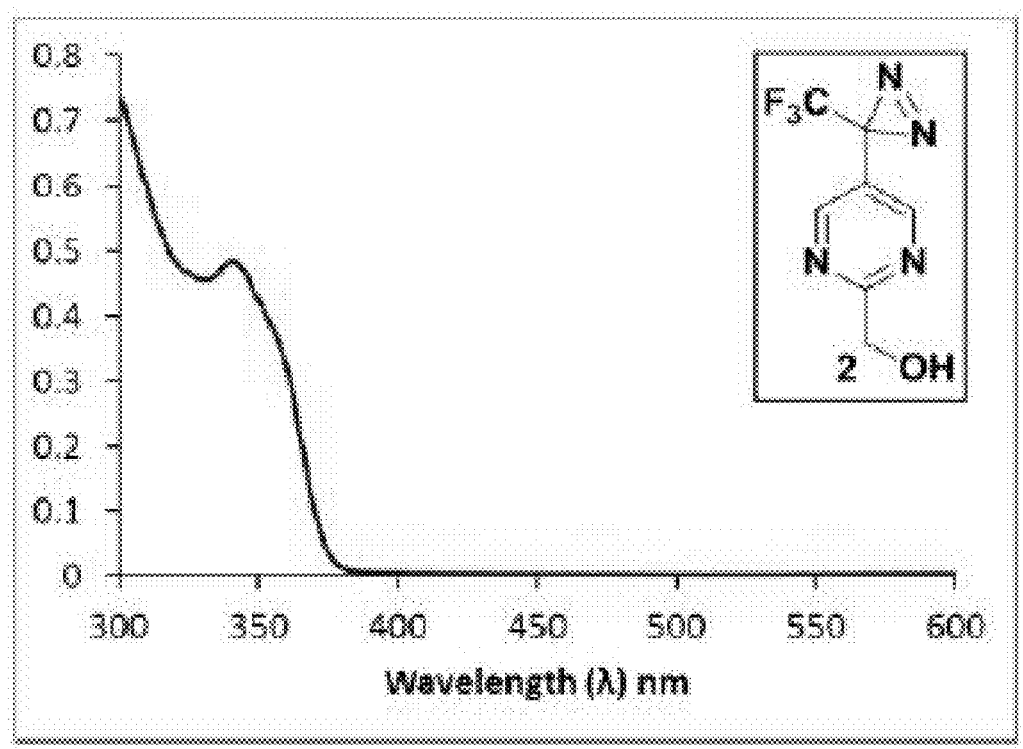

Finally, in order to determine the photolabeled site of Con A, samples photolabeled with 20-22 were subjected to trypsin digestion and subsequent analysis by liquid chromatography coupled to a linear ion trap-Orbitrap spectrometry. The labeled peptides with a neutral mass of 1826.9023, 1827.8971 and 1828.8940 Da, for the samples photolabeled with 20, 21 and 22 respectively, were found (FIG. 5A). Upon subtracting the mass of denitrogenated photolabels from the mass of labeled peptides, all the resultant masses corresponded to the mass of the peptide sequence Val91-Lys101 (VGLSASTGLYK) with high mass accuracy (<3 ppm) (FIG. 14). Further fragmentation of the labeled peptide in the Orbitrap mass spectrometer confirmed the identity and sequence of the labeled peptide (FIGS. 16-17). It is noteworthy that Hamachi and co-workers previously reported the same peptide sequence (Val91-Lys101) to be labeled, in their efforts to photolabel Con A with their 3-trifluoromethyl-3-phenyldiazirine derived photoaffinity label.[22] Computational modeling studies (FIG. 5B) revealed that the peptide sequence Val91-Lys101 forms the lip of the mannose binding pocket in Con A, accounting for the consistent labeling at this position. The mass spectroscopic analysis has confirmed that the ambient light stable pyridinyl and pyrimidinyl photolabels also undergoes the binding site specific labeling much like the conventional phenyl derived photolabels.

In sum, ambient light stable photolabels have been developed by substituting the phenyl ring in 3-trifluoromethyl-3-phenyldiazirine by a pyridine or pyrimidine ring in 3-position. Subsequent photoactivation and photoaffinity labeling studies of these pyridine or pyrimidine photolabels with Con A revealed that they are as efficient as the conventional 3-trifluoromethyl-3-phenyldiazirine probes. Furthermore, the pyridine and pyrimidine photolabels also showed significant aqueous solubility improvements over the conventional 3-trifluoromethyl-3-aryldiazirine photolabel. The favorable physicochemical properties including the improved ambient light stability of the pyridine and pyrimidine photolabels render significant advantages over the traditional 3-trifluoromethyl-3-aryldiazirine not only for the actual photolabeling experiment but also during the synthesis of the photoaffinity probes. We are currently investigating the possibility to use pyridine- and pyrimidine-substituted 3-trifluoromethyl-diazirines for the identification of biological targets associated to anti-malarial, anti-leishmanial and anti-bacterial agents.[23]

REFERENCES FOR EXAMPLE 1

1. J. Das, *Chem. Rev.* 2011, 111, 4405.
2. Z. Li, D. Wang, L. Li, S. Pan, Z. Na, C. Y. Tan, S. Q. Yao, *J. Am. Chem. Soc.* 2014, 136, 9990; E. Smith, I. Collins, *Future Med Chem* 2015, 7, 159.
3. Y. Hatanaka, Y. Sadakane, *Curr. Top. Med. Chem.* 2002, 2, 271.
4. F. Kotzybahibert, I. Kapfer, M. Goeldner, *Angew. Chem. Int. Ed. Engl.* 1995, 34, 1296.
5. G. Dorman, *Bioorg.* Chem. of Biol. Signal Transduction 2001, 211, 169; C. A. Gartner, *Curr. Med. Chem.* 2003, 10, 671.
6. H. Nakayama, Y. Hatanaka, M. Taki, E. Yoshida, Y. Kanaoka, *Ann. N. Y. Acad. Sci.* 1993, 707, 349.
7. J. Yang, A. E. Clark, I. J. Kozka, S. W. Cushman, G. D. Holman, *J. Biol. Chem.* 1992, 267, 10393.
8. J. J. Tate, J. Persinger, B. Bartholomew, *Nucleic Acids Res.* 1998, 26, 1421.
9. P. J. A. Weber, A. G. BeckSickinger, *J. Pept. Res.* 1997, 49, 375.
10. M. Hashimoto, Y. Hatanaka, *Eur. J. Org. Chem.* 2008, 2008, 2513.
11. L. Dubinsky, B. P. Krom, M. M. Meijler, *Bioorg. Med. Chem.* 2012, 20, 554.
12. B. L. Liu, D. S. Kang, *J. Chem. Inf. Comput. Sci.,* 1994, 34, 418; Y. G. He, C. P. Junk, J. J. Cawley, D. M. Lemal, *J. Am. Chem. Soc.* 2003, 125, 5590.
13. J. E. True, T. D. Thomas, R. W. Winter, G. L. Gard, *Inorg Chem* 2003, 42, 4437.
14. J. Brunner, H. Senn, F. M. Richards, *J. Biol. Chem.* 1980, 255, 3313.
15. B. Erni, H. G. Khorana, *J. Am. Chem. Soc.* 1980, 102, 3888; R. Bonneau, M. T. H. Liu, *J. Am. Chem. Soc.* 1996, 118, 7229; T. Akasaka, M. T. H. Liu, Y. Niino, Y. Maeda, T. Wakahara, M. Okamura; K. Kobayashi, S. Nagase, *J. Am. Chem. Soc.* 2000, 122, 7134; T. Wakahara, Y. Niino, T. Kato, Y. Maeda, T. Akasaka, M. T. H. Liu, K. Kobayashi, S. Nagase, *J. Am. Chem. Soc.* 2002, 124, 9465.
16. R. A. Moss, E. G. Jang, H. R. Kim, G. J. Ho, M. S. Baird, *Tetrahedron Lett.* 1992, 33, 1427; R. A. Moss, L. A. Perez, N. J. Turro, I. R. Gould, N. P. Hacker, *Tetrahedron Lett.* 1983, 24, 685; N. Soundararajan, M. S. Platz, J. E. Jackson, M. P. Doyle, S. M. Oon, M. T. H. Liu, S. M. Anand, *J. Am. Chem. Soc.* 1988, 110, 7143.
17. Z. Hasnik, P. Silhar, M. Hocek, *Synlett,* 2008, 2008, 543.
18. S. S. Husain, S. Nirthanan, D. Ruesch, K. Solt, Q. Cheng, G. D. Li, E. Arevalo, R. W. Olsen, D. E. Raines, S. A. Forman, J. B. Cohen, K. W. Miller, *J. Med. Chem.* 2006, 49, 4818.
19. A. B. Kumar, J. M. Anderson, R. Manetsch, *Org. Biomol. Chem.* 2011, 9, 6284; M. Daghish, L. Hennig, M. Findeisen, S. Giesa, F. Schumer, H. Hennig, A. G. Beck-Sickinger, P. Welzel, *Angew. Chem. Int. Ed. Engl.* 2002, 41, 2293.
20. Y. L. Zhang, G. Burdzinski, J. Kubicki, S. Vyas, C. M. Hadad, M. Sliwa, O. Poizat, G. Buntinx, M. S. Platz, *J. Am. Chem. Soc.* 2009, 131, 13784.
21. R. M. Cross, A. Monastyrskyi, T. S. Mukta, J. N. Burrows, D. E. Kyle, R. Manetsch, *J. Med. Chem.* 2010, 53, 7076.
22. T. Nagase, E. Nakata, S. Shinkai, I. Hamachi, *Chem. Eur. J.* 2003, 9, 3660.
23. K. S. Van Horn, W. N. Burda, R. Fleeman, L. N. Shaw, R. Manetsch, *J. Med. Chem.* 2014, 57, 3075; R. M. Cross, D. L. Flanigan, A. Monastyrskyi, A. N. LaCrue, F. E. Saenz, J. R. Maignan, T. S. Mutka, K. L. White, D. M. Shackleford, I. Bathurst, F. R. Fronczek, L. Wojtas, W. C. Guida, S. A. Charman, J. N. Burrows, D. E. Kyle, R. Manetsch, *J. Med. Chem.* 2014, 57, 8860; K. S. Van Horn, X. Zhu; T. Pandharkar, S. Yang, B. Vesely, M. Vanaerschot, J. C. Dujardin, S. Rijal, D. E. Kyle, M. Z. Wang, K. A. Werbovetz, R. Manetsch, *J. Med. Chem.* 2014, 57, 5141.
24. Kottani, R.; Valiulin, R. A.; Kutateladze, A. G., Direct screening of solution phase combinatorial libraries encoded with externally sensitized photolabile tags. *Proceedings of the National Academy of Sciences of the United States of America* 2006, 103, 13917-13921.
25. Habermeyer, B.; Takai, A.; Gros, C. P.; El Ojaimi, M.; Barbe, J. M.; Fukuzumi, S., Dynamics of Closure of Zinc Bis-Porphyrin Molecular Tweezers with Copper(II) Ions and Electron Transfer. *Chemistry—a European Journal* 2011, 17, 10670-10681.
26. Hasnik, Z.; Silhar, P.; Hocek, M., Hydroxymethylations of aryl halides by Pd-catalyzed cross-couplings with (benzoyloxy)methylzinc iodide—Scope and limitations of the reaction. *Synlett* 2008, 543-546.
27. Cross, R. M.; Monastyrskyi, A.; Mukta, T. S.; Burrows, J. N.; Kyle, D. E.; Manetsch, R., Endochin Optimization: Structure-Activity and Structure-Property Relationship Studies of 3-Substituted 2-Methyl-4(1H)-quinolones with Antimalarial Activity. *Journal of Medicinal Chemistry* 2010, 53, 7076-7094.

We claim:

1. A compound having a structure according to Formula A

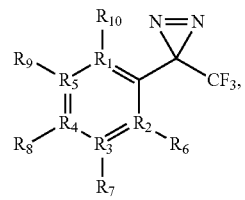

Formula A wherein $R_1$, $R_2$, $R_3$, $R_4$, and $R_5$, are each independently selected from the group consisting of: C and N, wherein at least one of $R_1$, $R_2$, $R_3$, $R_4$, and $R_5$, is N, wherein $R_6$, $R_7$, $R_8$, $R_9$, and $R_{10}$ are each independently selected from the group consisting of H, —OH, and an alkyl alcohol, and wherein at least one of $R_6$, $R_7$, $R_8$, $R_9$, and $R_{10}$ is an —OH or an alkyl alcohol.

2. The compound of claim 1, wherein at least two of $R_1$, $R_2$, $R_3$, $R_4$, and $R_5$, is N.

3. The compound of claim 2, wherein $R_3$, and $R_5$, are N.

4. The compound of claim 2, wherein $R_8$ is an alkyl alcohol.

5. The compound of claim 2, wherein the compound has a structure according to Formula 2

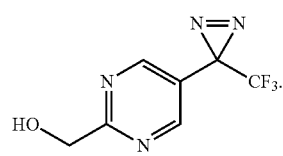

Formula 2

6. The compound of claim 1, wherein $R_5$, is N.

7. The compound of claim 6, wherein $R_8$ is an alkyl alcohol.

8. The compound of claim 6, wherein the compound has a structure according to Formula 1

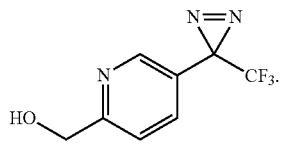

Formula 1

9. A method of preparing a photoaffinity label, the method comprising;
   coupling a photoaffinity tag to a compound having a structure according to Formula A

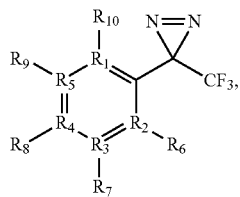

Formula A wherein $R_1$, $R_2$, $R_3$, $R_4$, and $R_5$, are each independently selected from the group consisting of: C and N,
wherein at least one of $R_1$, $R_2$, $R_3$, $R_4$, and $R_5$, is N,
wherein $R_6$, $R_7$, $R_8$, $R_9$, and $R_{10}$ are each independently selected from the group consisting of H, —OH, and an alkyl alcohol, and
wherein at least one of $R_6$, $R_7$, $R_8$, $R_9$, and $R_{10}$ is an —OH or an alkyl alcohol.

10. The method of claim 9, wherein at least two of $R_1$, $R_2$, $R_3$, $R_4$, and $R_5$, is N.

11. The method of claim 10, wherein $R_3$, and $R_5$, are N.

12. The method of claim 10, wherein $R_8$ is an alkyl alcohol.

13. The method of claim 2, wherein the compound having a structure according to Formula A has a structure according to Formula 2

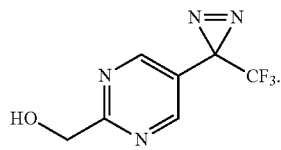

Formula 2

14. The method of claim 9, wherein $R_5$, is N.

15. The method of claim 14, wherein $R_8$ is an alkyl alcohol.

16. The method of claim 14, wherein the compound having a structure according to Formula A has a structure according to Formula 1

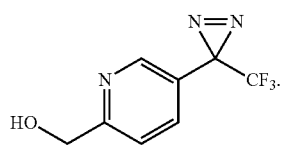

Formula 1

17. The method of claim 9, further comprising coupling a ligand of a protein to the compound having a structure according to Formula A.

18. The method of claim 17, further comprising the step of contacting the compound having a structure according to Formula A that is coupled to a photoaffinity tag and ligand with a protein.

19. The method of claim 9, further comprising coupling a protein to the compound having a structure according to Formula A.

20. The method of claim 9, wherein the photoaffinity tag is selected from the group consisting of: biotin, His-tag, FLAG, Streptag II, hemagllutinin (HA)-tag, Softag1, Softag3, c-myc, T7-tag, S-tag, Elastin-like peptides, Chitin-binding domain, Thioredoxin, Xylanase 10A, Glutathione S-transferase, Maltose binding protein, NusA, any amine derivative thereof, and any combinations thereof.

* * * * *